US011718819B2

United States Patent
Xia et al.

(12)

(10) Patent No.: US 11,718,819 B2
(45) Date of Patent: Aug. 8, 2023

(54) CELL PROLIFERATION BIOREACTOR

(71) Applicant: Shanghai Longevity Co., Ltd., Shanghai (CN)

(72) Inventors: Tian Xia, Shanghai (CN); Ke Ma, Shanghai (CN)

(73) Assignee: Shanghai Longevity Co., Ltd., Shanghai (CN)

( * ) Notice: Subject to any disclaimer, the term of this patent is extended or adjusted under 35 U.S.C. 154(b) by 0 days.

(21) Appl. No.: 17/500,869

(22) Filed: Oct. 13, 2021

(65) Prior Publication Data

US 2023/0090147 A1    Mar. 23, 2023

(30) Foreign Application Priority Data

Sep. 22, 2021    (WO) ............... PCT/CN2021/119701

(51) Int. Cl.
| | | |
|---|---|---|
| *C12M 1/36* | (2006.01) | |
| *C12M 1/26* | (2006.01) | |
| *C12M 1/12* | (2006.01) | |
| *C12M 3/00* | (2006.01) | |
| *C12M 1/00* | (2006.01) | |

(52) U.S. Cl.
CPC ............ *C12M 41/48* (2013.01); *C12M 23/22* (2013.01); *C12M 23/48* (2013.01); *C12M 25/02* (2013.01); *C12M 33/00* (2013.01)

(58) Field of Classification Search
CPC ...... C12M 41/48; C12M 23/22; C12M 23/48; C12M 25/02; C12M 33/00
See application file for complete search history.

(56) References Cited

U.S. PATENT DOCUMENTS

| | | |
|---|---|---|
| 2010/0311146 A1 | 12/2010 | Auton |
| 2014/0273077 A1 | 9/2014 | Knaus et al. |
| 2016/0053213 A1 | 2/2016 | Hedberg |
| 2019/0094208 A1 | 3/2019 | Vuong et al. |
| 2020/0024561 A1 | 1/2020 | Naing et al. |
| 2020/0080045 A1* | 3/2020 | Bernate ................. C12M 33/14 |

FOREIGN PATENT DOCUMENTS

CN          214193294 U       9/2021

OTHER PUBLICATIONS

International Search Report and Written Opinion of the International Searching Authority for International Patent Application No. PCT/CN2022/120661, dated Dec. 15, 2022, 9 pages.

* cited by examiner

*Primary Examiner* — Lydia Edwards

(57) ABSTRACT

A bioreactor includes a culture medium vessel housing culture medium. The culture medium vessel further includes a first side surface including a first transparent optical window; and a second side surface parallel to the first surface and including one or more sensor adapters to fix optical sensors. A cell retention vessel is disposed underneath and connected to the culture medium vessel, the cell retention vessel housing biological cells and having: a top surface that intersects a base of the culture medium vessel, and a second transparent optical window indented into the top surface at a first corner of the top surface. A semipermeable membrane is disposed at a bottom of the cell retention vessel, and a frame comprising a grid is disposed underneath the semipermeable membrane.

20 Claims, 14 Drawing Sheets

CELL PROLIFERATION BIOREACTOR

CROSS REFERENCE TO RELATED APPLICATIONS

This application claims priority to PCT/CN2021/119701, filed Sep. 22, 2021, the entirety of which is incorporated herein.

BACKGROUND

A cellular therapy process involves obtaining tissue samples, isolating cells from the tissue samples, culturing and expanding the cells, and harvesting or preserving the cells. During the cell culture and expansion steps, bioreactors support and maintain growth of organisms such as cells or tissues within a controlled environment. Inside the bioreactors, the organisms may be supplied growth essentials such as nutrients, metabolites, and oxygen while being maintained in an environment under certain gas exchange, pH and temperature conditions. Because conditions within the bioreactors profoundly impact cell growth and expansion, the conditions must be tightly controlled.

Specific categories of bioreactors include stirred tanks, fixed and packed beds, rocking platforms, and hollow fiber systems. These bioreactors exhibit distinctions regarding geometry and fluid agitation methods. Determining which bioreactor to use depends on culture conditions required for the cells of interest. For example, stirred tanks and rocking platforms may be applied to non-adherent, suspension cell types, but not to cell types requiring an adherent surface and unperturbed culturing conditions. For the latter cell types, hollow fibers and fixed or packed beds may be more conducive.

SUMMARY

Described herein, in some embodiments, is a bioreactor that operates according to Process Analytical Technology (PAT) principles. The bioreactor may include a single-use bioreactor (SUB) used to expand a concentration or density of cells in any cell culture process, such as T cells, TCR-T cells, CAR-T cells, nature killer (NK) cells or Monocyte-derived Dendritic cells (Mo-DC) or mesenchymal stem or stromal cells for tissue regeneration or graft-versus-host disease therapy, might previously harvested from a primary culture process or initiated from cell-free liquid samples or seeds. The cells may expansively grow in the bioreactor by consuming nutrients and dissolved oxygen contained in the culture medium, thereafter, producing metabolites which interact with and alter the physical, chemical, and biological parameters of the culture medium. PAT sensors may be integrated with the bioreactor to perform In-line or in-situ, and/or online monitoring, rather than off-line monitoring, of critical process parameters (CPPB) such as overall or total cell density, viable cell density, pH, $pO_2$, $pCO_2$, temperature, pressure, oxidation reduction potential (ORP), glucose, glutamine, lactate, ethanol, and/or ammonium. Such monitoring and quality analysis improve the understanding, control, and optimization of cell expansion process and eventual cell density or yield to inform a decision-making process during cell culture procedures and techniques. As a result, growth conditions within the bioreactor may be kept uniform and consistent, improved, and optimized. Following growth and/or expansion in the bioreactor, the cells may be harvested from the SUB and injected to patients for type-specific cancer immuno therapy.

A bioreactor includes a culture medium vessel housing culture medium. The culture medium vessel further includes a first side surface including a first transparent optical window; and a second side surface parallel to the first surface and including one or more sensor adapters to fix optical detectors. A cell retention vessel is disposed underneath and connected to the culture medium vessel, the cell retention vessel housing biological cells and having: a top surface that intersects a base of the culture medium vessel, and a second transparent optical window indented into the top surface at a first corner of the top surface. A semipermeable membrane is disposed at a bottom of the cell retention vessel, and a frame comprising a grid is disposed underneath the semipermeable membrane.

In some embodiments, the cell retention vessel has a larger width and a smaller height compared to the culture medium vessel in order to support a larger surface area on which the biological cells suspend and grow.

In some embodiments, the culture medium vessel comprises a third side surface from which interfaces extend, wherein the third side surface is parallel to each other and orthogonal to the first side surface and the second side surface.

In some embodiments, the interfaces comprise Luer connectors.

In some embodiments, the culture medium vessel further comprises: a top surface; and extending from the top surface, a culture medium injection interface through which culture medium is injected into the culture medium vessel.

In some embodiments, the culture medium vessel further comprises: extending from the top surface, one or more sampling interfaces from which liquid samples contained in the culture medium vessel or the cell retention vessel are extracted for in-line process analytical technology (PAT) analysis.

In some embodiments, the sampling interfaces comprise a first sampling interface from which a sample inside the culture medium vessel is extracted and a second sampling interface from which a sample inside the cell retention vessel is extracted.

In some embodiments, the interfaces comprise one or more waste collection interfaces through which culture medium is determined expelled or detrimental to cell growth.

In some embodiments, the cell retention vessel comprises one or more second sensor adapters extending from the top surface of the cell retention vessel, wherein the second sensor adapters are configured to fix second optical sensors.

In some embodiments, the optical sensors comprise fluorescence quenching sensor spots vertically translatable along the sensor adapters.

In some embodiments, an interior of the bottom of the culture medium vessel is hollowed. The interior of the bottom of the culture medium vessel may coincide with an interior portion of the top surface of the cell retention vessel.

In some embodiments, the cell retention vessel further comprises: a side surface; and extending from the side surface, a cell harvest interface from which a subset of the biological cells is transferred to be harvested upon a threshold cell density of the biological cells being detected within the cell retention vessel.

In some embodiments, the cell retention vessel further comprises: extending from the top surface of the cell retention vessel, cell injection interfaces through which the biological cells sinking in the culture medium are injected into the cell retention vessel.

In some embodiments, the top surface of the cell retention vessel comprises four orthogonal sides and a hollowed interior region to an interior of the bottom of the culture medium vessel; and the cell injection interfaces are disposed on the middle region of different sides of the top surface of the cell retention vessel.

An assembly includes a bioreactor configured to grow cells, the bioreactor including: a culture medium vessel; a cell retention vessel beneath the culture medium vessel; and a semipermeable membrane at a bottom of the culture medium vessel. The assembly includes one or more processors; and a memory storing instructions that, when executed by the one or more processors, cause the one or more processors to: determine one or more parameters associated with a cell density within the cell retention vessel and with a culture medium within the culture medium vessel or the cell retention vessel; based on the one or more PAT parameters, determine a status of culture medium expulsion or injection; and based on the status, actuate one or more connectors associated with a culture medium injection or sampling or waste collection interface of the culture medium vessel.

In some embodiments, the status comprises an indication of whether or not the culture medium is to be injected or expelled or a batch timing at which the culture medium is to be injected or expelled.

In some embodiments, the PAT-based predictive instructions further cause the one or more processors to: based on the one or more parameters, determine a status of a cell injection or a cell harvest; and based on the status, actuate one or more connectors associated with a cell harvest interface or a cell injection interfaces of the cell retention vessel.

In some embodiments, the PAT parameters associated with the culture medium comprise any of a pH, $pO_2$, or $pCO_2$.

In some embodiments, the parameters associated with the biomass comprise a total cell density or a viable cell density.

These and other features of the bioreactors, apparatuses, systems, assemblies, methods, processors, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

FIG. 2 has been rotated by approximately 90 degrees clockwise about the z-axis compared to FIG. 1.

illustrates a front perspective, or isometric, view of an exemplary bioreactor, including a support for a semipermeable membrane, in accordance with various embodiments.

Figure 10:
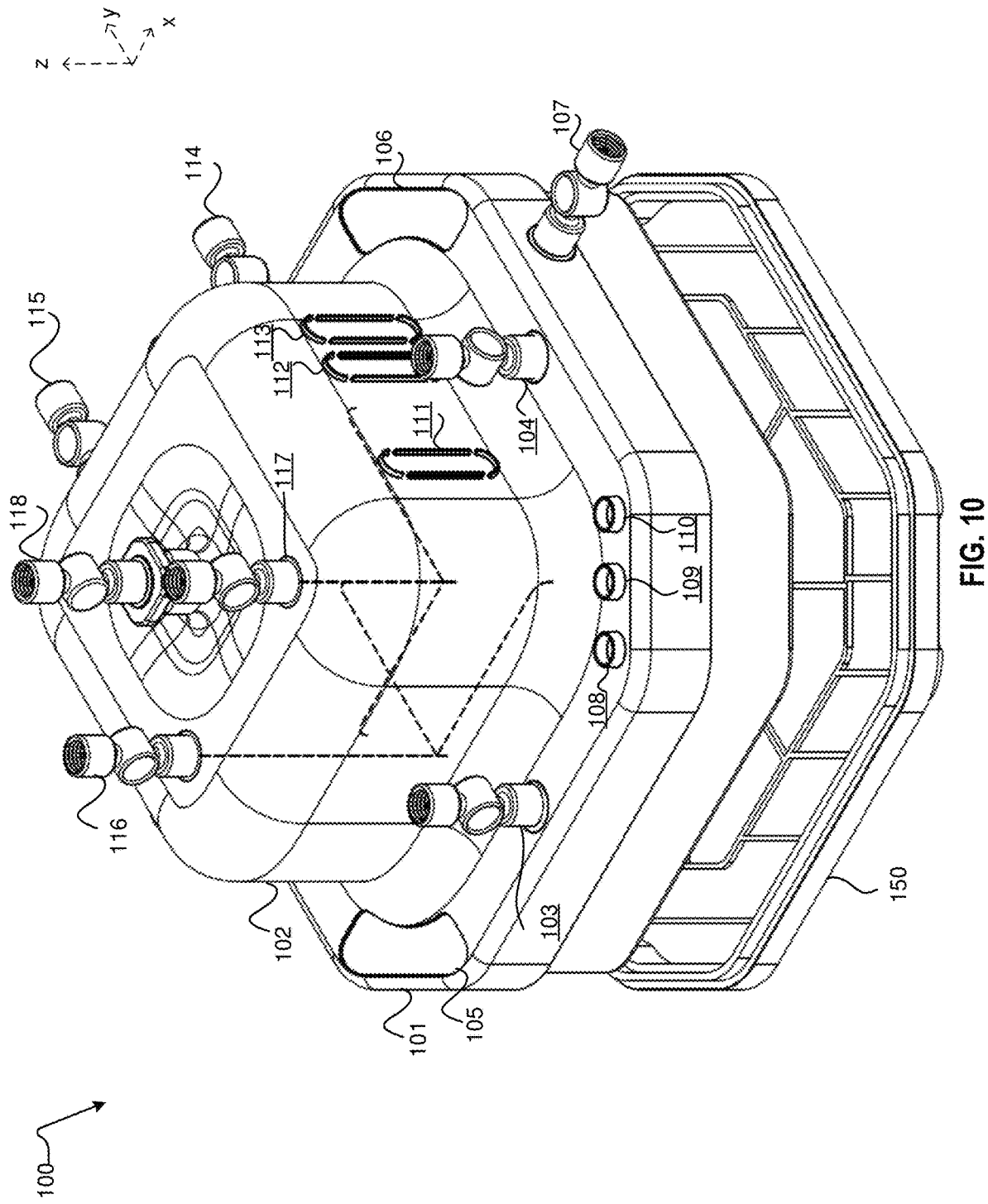

FIG. 10 illustrates a front perspective, or isometric, view of an exemplary bioreactor, including a support for a semipermeable membrane, in accordance with various embodiments.

Figure 11:
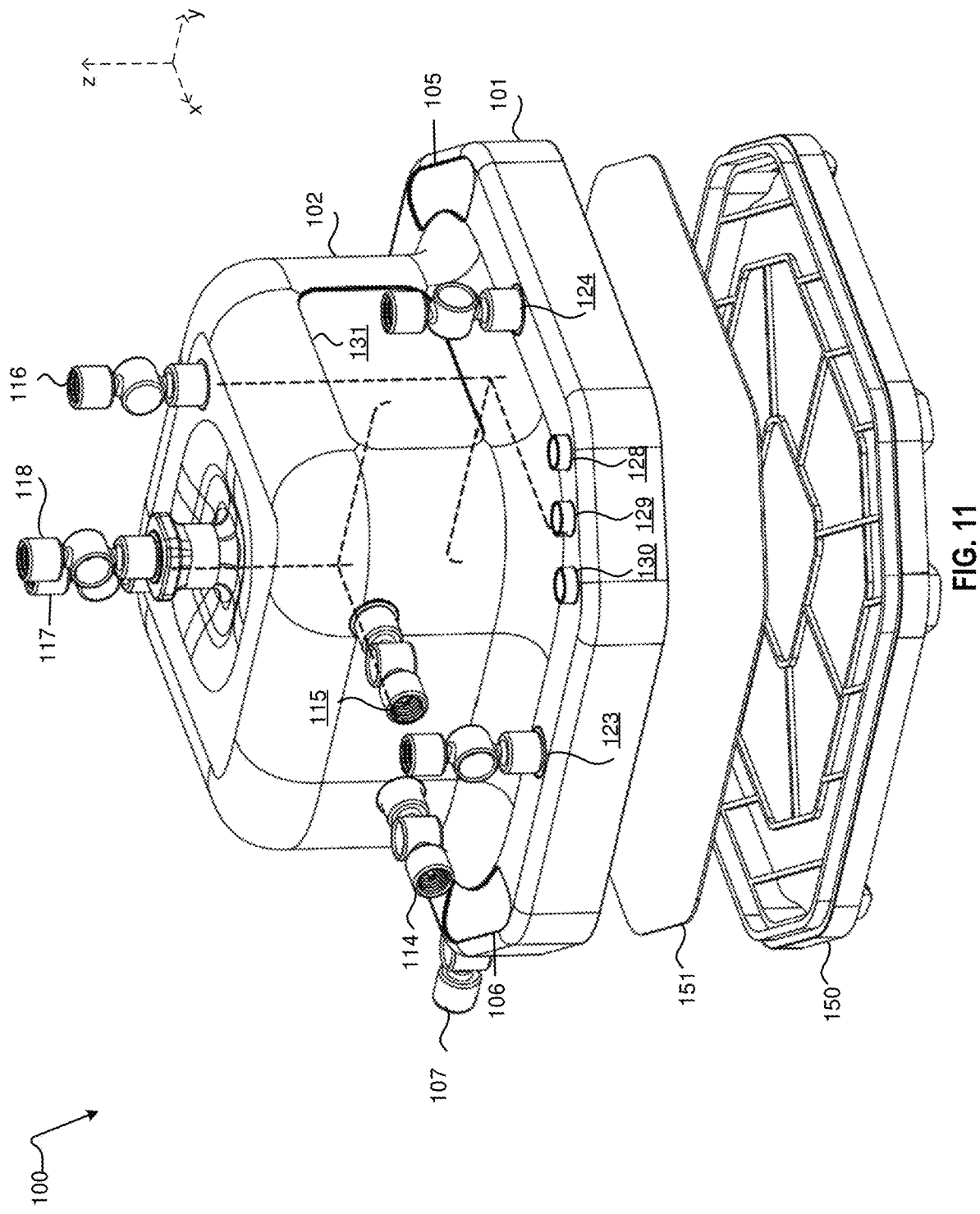

FIG. 11 illustrates a back perspective, or dimetric, view of an exemplary bioreactor, including a support for a semipermeable membrane, in accordance with various embodiments.

Figure 12:
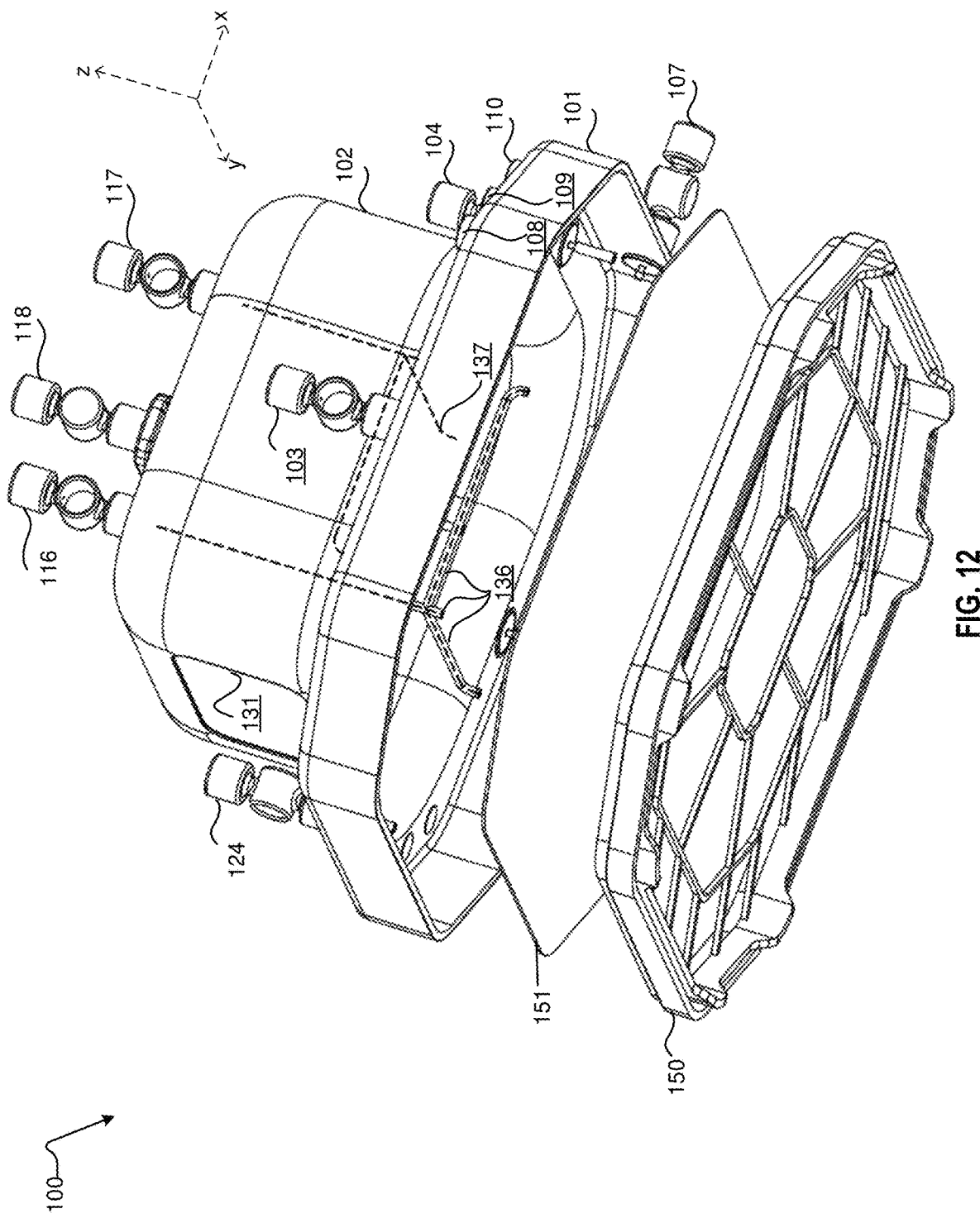

FIG. 12 illustrates a perspective, or trimetric, view of an exemplary bioreactor, including a support for a semipermeable membrane, in accordance with various embodiments.

Figure 13:
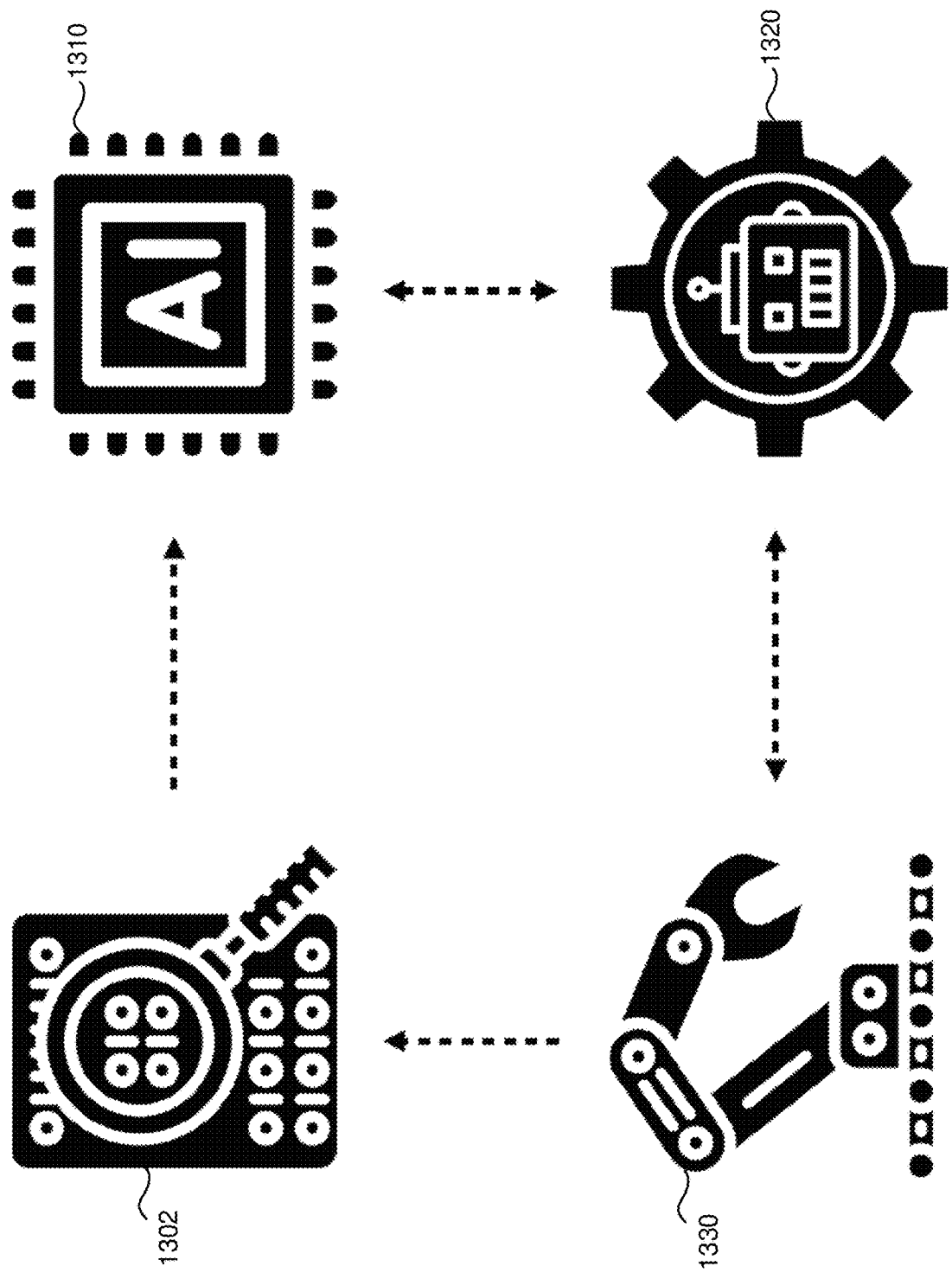

FIG. 13 illustrates an exemplary PAT framework diagram illustrating PAT analysis of parameters or conditions within an exemplary bioreactor as illustrated in FIGS. 1-12.

Figure 14:
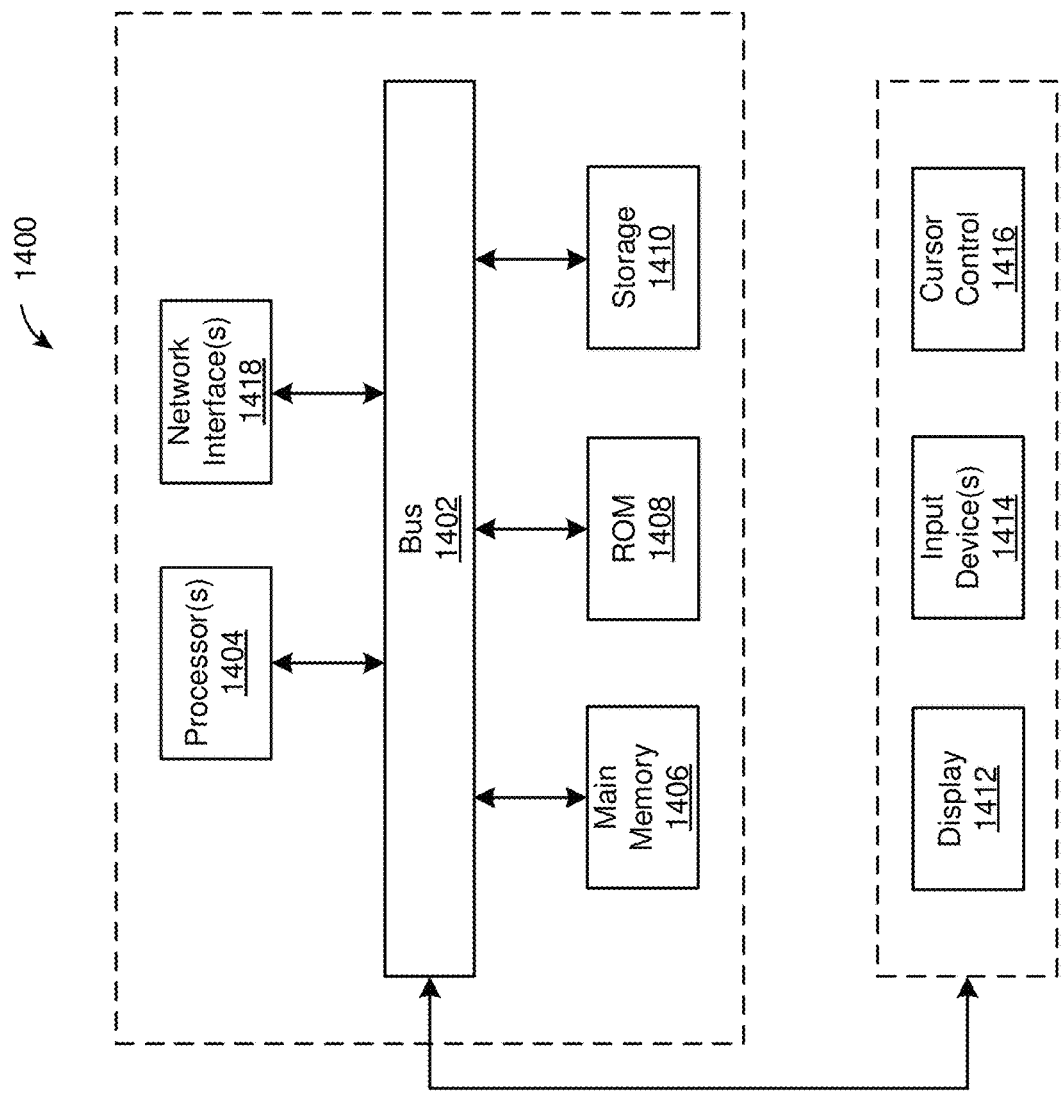

FIG. 14 is a schematic block diagram of a computer system upon which any of the embodiments described herein may be implemented.

Descriptions and principles associated with each of the figures may apply to other figures.

DETAILED DESCRIPTION

PAT is an initiative by the United States Food and Drug Administration (FDA), originated in 2004, to design, analyze, and control biopharmaceutical manufacturing processes via a continuous measurement of CPPs of equipment to control critical quality attributes (CQAs) of a final product. A goal of PAT is to control the CPPs to be within defined limits by compensating for variability in raw materials and equipment. A PAT-based approach of an analytical instrument involves analysis of biological data to determine the CPPs, in-line and on-line analytical instruments to measure the determined CPPs, and continuous improvement mechanisms.

Principles of PAT may be applied to equipment implemented in development of cell-based therapies such as chimeric antigen receptor (CAR)- and T-cell receptor (TCR)-engineering techniques. The equipment may encompass bioreactors to culture various types of cells. According to these principles, PAT sensors may be connected and in communication with the equipment. Data that is continuously obtained by the sensors may be analyzed to elucidate, control, and optimize decision-making processes of cell culture procedures and techniques.

Cell culture containers may enclose an environment with culture medium and oxygen in order to facilitate cell proliferation. Shortcomings of current cell culture containers include limited ability to adjust culture conditions, and insufficient capabilities of on-line and in-line monitoring of the wide range of parameters (e.g., CPPs) while maintaining a closed, sterile system. For example, current techniques of monitoring parameters may require samples of cells may need to be withdrawn and analyzed outside of the containers using an at-line or off-line analysis. As a result, not only might the density of the cells be reduced from having to remove samples of cells, but the growth of the cells may also be compromised by contamination to air and foreign matter such as viruses or bacteria. In addition, the constant exposure to the air may also render the growth conditions inconsistent over time. Because the growth of the cells includes many rounds of multiplication in order to obtain a feasible concentration or number of cells, a cumulative effect of transporting cells outside of the bioreactor may result in prolonged exposure to contaminants. More importantly, the at-line or off-line analysis cannot represent the real-time actual state of the bioreactor, which results in imprecise understanding of the bioprocess variables and hinders a goal of fulfilling PAT objectives. In-line and on-line analysis for real-time monitoring would therefore enhance an accuracy of monitoring the bioprocess variables and improve cell proliferation, uniformity, and quality.

A bioreactor, such as a SUB, according to present embodiments, continuously monitors, detects, and adjusts growth conditions using PAT sensors and automatic control of injection and/or expulsion of substances such as growth medium. The bioreactor may be bound by a wall. The wall may include five surfaces, including a top flat surface, a concave curved surface within a center of the top flat surface, and four flat side surfaces. Transitional interfaces between the flat surface and the side surfaces may include curvatures. Radii of the curvatures may range from one-quarter to three-quarters of a dimension (e.g., width) of a top flat surface. Additionally, transitional interfaces between adjacent side surfaces may be curved. The concave curved surface may provide a remaining buffer space to connect with liquid injection Luer connectors such as culture medium injection interfaces.

The side walls may provide supports or frameworks to attach non-invasive sensors used to perform PAT data monitoring. Two types of non-invasive sensor accessories, fluorescence quenching sensor spots and optical detection windows, may be located at designated positions of the side walls. Three sensor spots, which may be shaped as rounded stripes, may be attached in an interior of one side surface in a vertical array. The sensor spots may assist optical probes or meters in examining pH, partial pressure of oxygen ($pO_2$), and partial pressure of carbon dioxide ($pCO_2$) of the culture medium using optical technologies such as fluorescence quenching.

Additionally, one or split optical windows are located on one side flat surface, leaving proper margins to the rounded edge of the side wall. Specifically, the optical window is pure transparent, particularly having thinner thickness rather than the wall, to provide a precise optical medium for the non-invasive spectroscopic sensors. The optical window is spaced apart from, and does not contact, the sensor and analytes in the culture medium while delivering and receiving optical signals.

Sensor adapters may be positioned at, or slightly over a surface of, walls of the bioreactor to affix the optical sensors by holding an optical detector, which may include a polymer optical fiber (POF), at locations of the sensor spots. The adapters may have a common edge size relative to the sensor spots and a raised frame to circumscribe the POF. The optical signal may be transmitted from the POF through the corresponding walls of the bioreactor, to the sensor spots, and the culture medium to detect biological components. The sensor adapters may permit the POF to slide up and down in order to flexibly locate and capture analytes within the culture medium vessel. The POF may determine, for example, levels of pH and dissolved gasses.

Generally, the bioreactor may be in a jellyfish-like form that generally houses cells, culture medium, and gas. The bioreactor may be divided into three sections, including a culture medium vessel on top, a cell retention vessel, and a semi-permeable membrane at a bottom. In the bioreactor, a transparent wall may block an external environment and may be analogous to a skin of a jellyfish. The transparent wall may maintain an internal environment within the bioreactor as a closed system. The bioreactor also includes input/output (I/O) Luer interfaces or connectors (hereinafter "connectors") that connect to PAT sensors and external devices. The connectors may be analogous to tentacles of a jellyfish to interact with PAT sensors and external devices. The connectors may include female adapters and/or threaded regions through which male adapters connect to form a closed protection. The semi-permeable membrane may be disposed at a bottom of the bioreactor and used to exchange gases. In some embodiments, a total volume of the bioreactor may be 5 Liters (L). Injection of culture medium within the bioreactor may be semi-continuous, which is not determined with a fixed batch and otherwise may be based on measured CPPs, in some embodiments. For example, a rate and/or an amount of the culture medium within the bioreactor may be regulated based at least in part on the measured CPPs.

Luer connectors or interfaces are equipped as I/O ports to communicate with peripheral devices including automated pipette or pumper, PAT sensors or analyzers, SUBs, and automated or robotic systems. The Luer connectors or interfaces are part of a standard closed system protocol to maintain the sterility, compatibility, and immobility in the process of interaction with the aforementioned devices. In particular, one medium injection connector and two sampling connectors are immobilized on the top flat surface. A medium injection connector or interface is located at a center of the top flat surface while two sampling connectors are disposed beside, and spaced apart from, the medium injection connector or interface. Two waste liquid handling connectors are located on one side surface, connecting with a waste displacing device or container. Through the interfaces, pipes or tubes (hereinafter "pipes") having specific liquid handling functionalities are implanted within the vessel. A liquid injection pipe may be used to transport the culture medium from external devices such as a pipette or a pump-based medium exchanger into the bioreactor. Meanwhile, one or more medium sampling pipes may be used to extract samplings of the culture medium to external devices such as PAT analyzers or other PAT probes for in-line analysis. A number of medium sampling pipes may be any suitable number, such as two or four. The medium sampling pipes may extend approximately halfway down the culture medium vessel and may bifurcate into multiple branches. The endpoints of the branches correspond to distinct, distributed locations of the culture medium to be sampled, in order to acquire an average composition of the culture medium and reduce or eliminate bias caused by imbalances within the culture medium. For example, the medium sampling pipes may bifurcate into four different branches. Further elaboration will be provided with respect to the FIGURES below.

Figure 1:
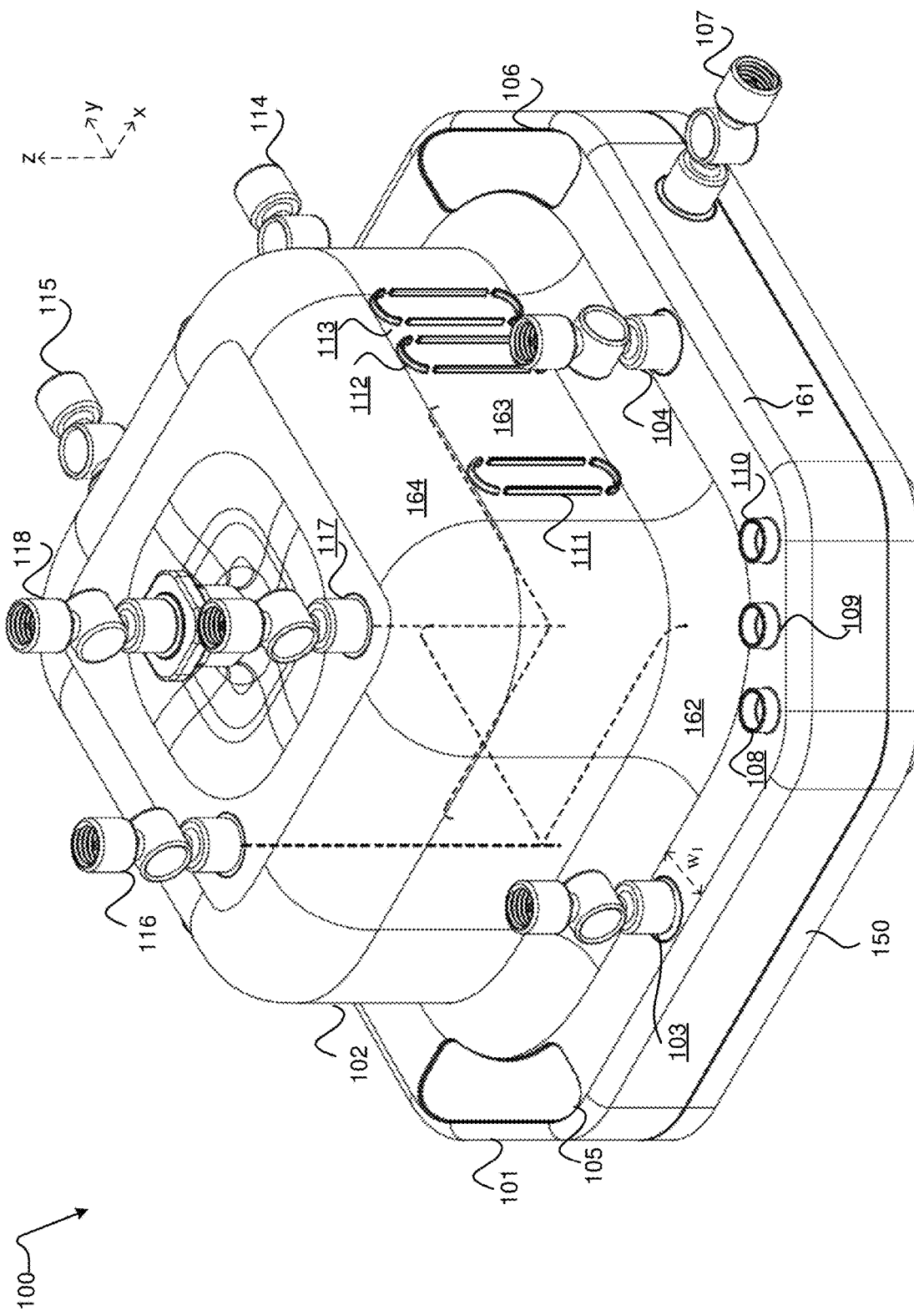
FIG. 1 illustrates a front perspective, or isometric, view of an exemplary bioreactor, in accordance with various embodiments.
Figure 2:
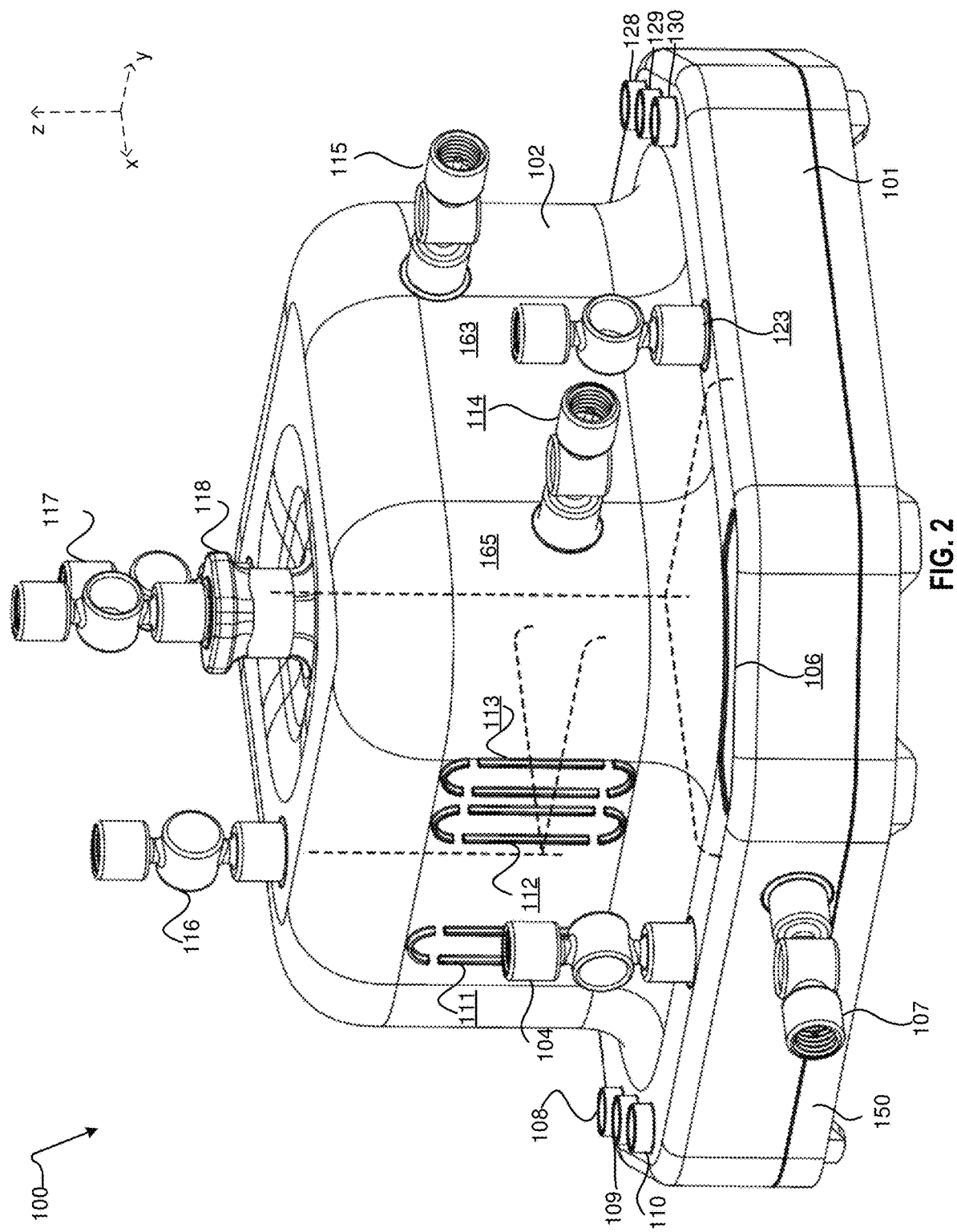
FIG. 2 illustrates a right-side perspective, or dimetric, view of an exemplary bioreactor, in accordance with various embodiments.

FIG. 1 illustrates an exemplary bioreactor 100 that includes three sections, a culture medium vessel 102 that houses culture medium, a cell retention vessel 101 in which cells are localized, and disposed underneath the culture medium vessel 102, and a support 150 that upon which a semi-permeable membrane 151 is placed. The support 150 may include a grid and a supporting framework. The grid may include thousands of pores to permit an ingress of gas while sparing a partial weight load of liquids within the bioreactor 100. The supporting framework may stabilize the semi-permeable membrane and the bioreactor 100. Brackets may be positioned at a bottom of the supporting framework to raise a level of the semi-permeable membrane 151 to a mid-air height, thereby leaving space for gas exchanges. The cell retention vessel 101, the culture medium vessel 102, and the support 150 may be integrated. The culture medium vessel 102 may take up a majority of a total volume of the bioreactor 100, for example, approximately 80% of a total volume of the bioreactor 100 or between 60% and 90% of the total volume. The cell retention vessel 101 may be responsible for preserving viable cells within the culture medium. Cells may be growing in a state of suspension near a bottom surface of the cell retention vessel 101. The cell retention vessel 101 may have a larger width or diameter and a smaller height compared to that of the culture medium vessel 102 so that the cells may have a larger surface area to suspend and grow on. The cell retention vessel 101 may have a cross-section, along a xy-plane, that resembles or be is shaped as an octagon, containing four straight edges and four slanted edges. Boundaries or intersections between the straight edges and the slanted edges may include fillets or curvatures. The lengths of the straight edges may be greater than the slanted edges. An intersecting interface between the culture medium vessel 102 and the cell retention vessel 101, between a transition 162 and a top surface of the cell retention vessel 101, may form a flat surface of a hollowed or an indented octagon of smaller dimensions compared to the octagon of the cross-section of the cell retention vessel 101. The transition 162 may be at a bottom of the culture medium vessel 102. A distance or width, $w_1$, between an internal edge of the hollowed octagon and an external edge of the octagon forming the cross-section may be uniform. Due to the hollowed or indented octagon, pipes from the medium injection connector and the liquid handling connectors may traverse the culture medium vessel 102 to the cell retention vessel 101 without any physical barriers between the culture medium vessel 102 and the cell retention vessel 101. Therefore, analysis of, or between, parameters within the culture medium vessel 102 and the cell retention vessel 101 may be conducted conveniently at a same time instance. The simultaneous and seamless analysis both within the culture medium vessel 102 and the cell retention vessel 101 enhances functionality of PAT analysis of the culture medium and the cultured cells.

Figure 9:
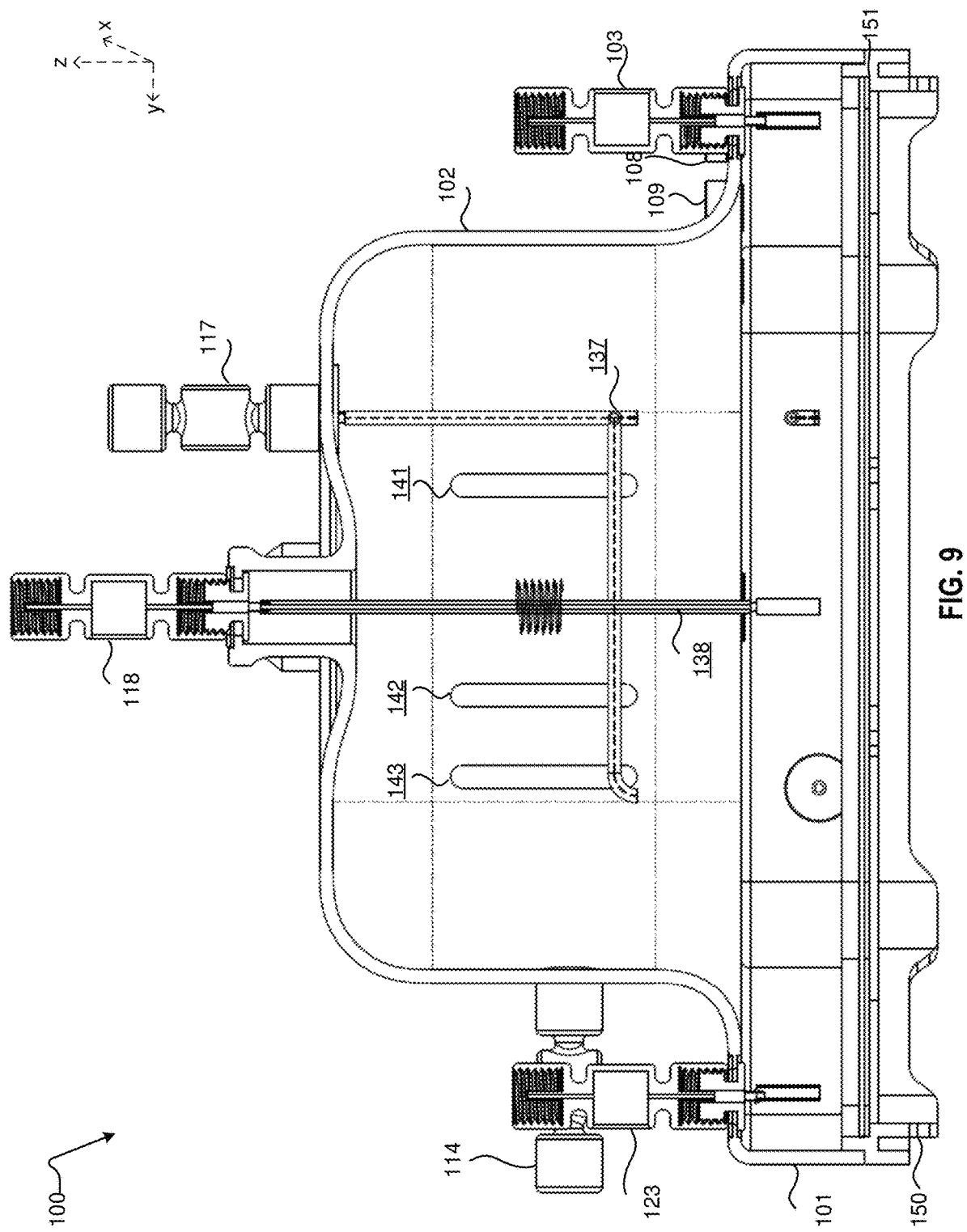
FIG. 9 illustrates an elevation, or orthographic, view of a left side of an exemplary bioreactor, in accordance with various embodiments.

In some embodiments, a diameter of the cell retention vessel 101 may be between from about 1 and 1.5 times a diameter of the culture medium vessel 102, and a height of the cell retention vessel 101 may be from about 0.1 and 0.3 times a height of the culture medium vessel 102. The semi-permeable membrane 151 is illustrated in FIGS. 9, 11, and 12, and facilitates gas exchange. In particular, the semi-permeable membrane 151 rests atop the support 150 and contains pores through which gasses, such as oxygen, are transferred into the cell retention vessel 101, where the gasses are dissolved. The oxygen passes into cells while carbon dioxide and other waste gases are transferred out of cells. For example, gasses may be exchanged from underneath the semi-permeable membrane 151 to above the semi-permeable membrane 151. The semi-permeable membrane 151 may cover an entire area of the support 150. The semi-permeable membrane 151 may include a waterproof PTFE material and may further filter out harmful or superfluous substances. The cells may grow and suspend on top of the semi-permeable membrane 151.

Figure 8:
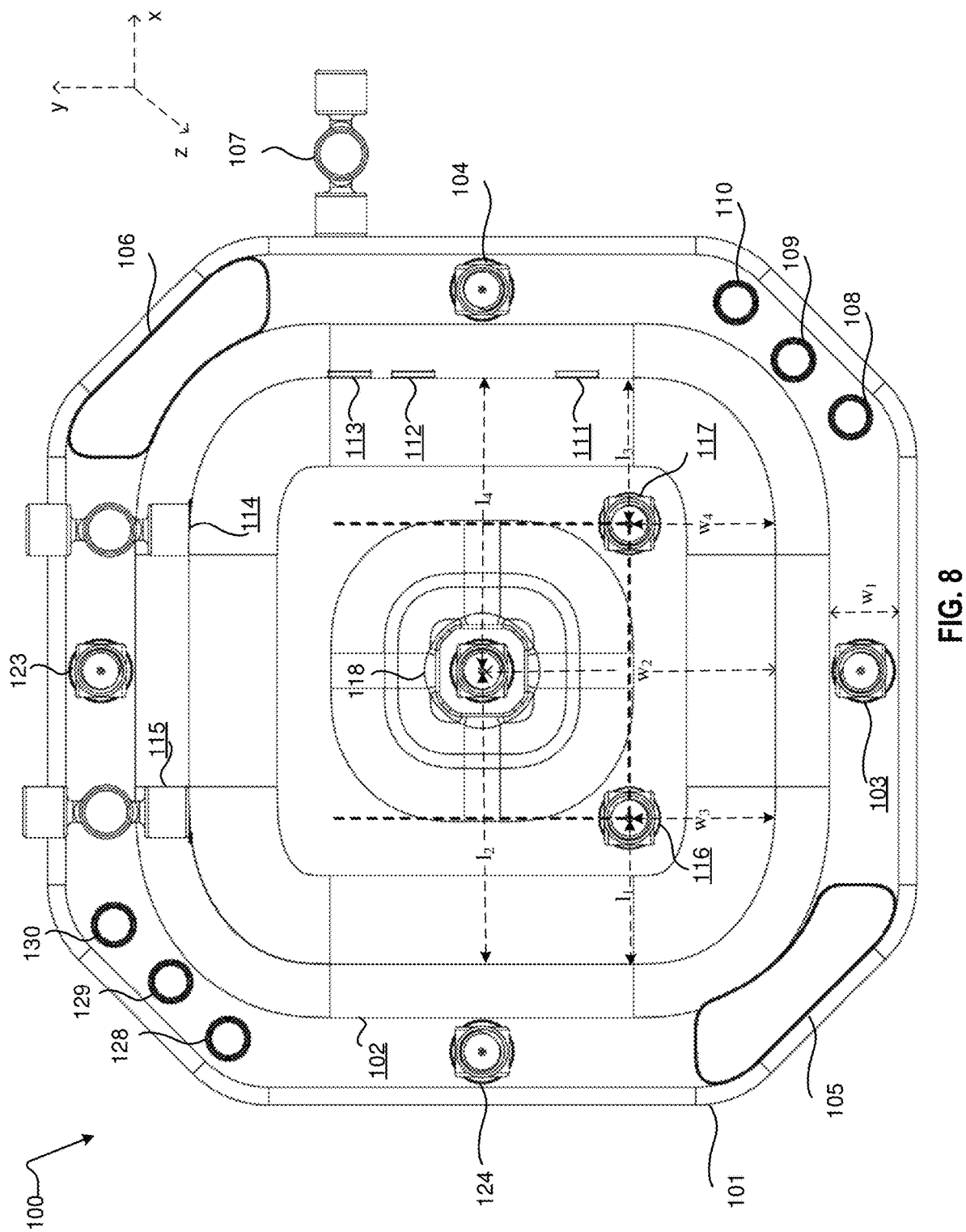
FIG. 8 illustrates a plan view of an exemplary bioreactor, in accordance with various embodiments.

The cell retention vessel 101 may facilitate a measurement of parameters (e.g., CPPs), injection of cells, and harvesting of cells within a closed system. A top of the cell retention vessel 101 may include a flat section having a constant or relatively constant width $w_1$, and curved or rounded edges or corners having a nonconstant width smaller than $w_1$, for example, ranging from approximately 50% to 80% of $w_1$, as illustrated in FIGS. 1 and 8. Referring to the cell retention vessel 101, optical windows 105 and 106 are disposed on opposite (e.g., diagonal) corners, as illustrated in FIGS. 1, 2, 7, 8, 10, and 11. The optical windows 105 and 106 may be shaped as or resemble a bow having rounded corners. The optical windows 105 and 106 may extend from an interior of the cell retention vessel 101 to a boundary of the culture medium vessel 102 and may include rounded edges. For example, the optical windows 105 and 106 may directly abut a curved edge or fillet (hereinafter "fillet") 161 and a curved edge, fillet, or transition (hereinafter "transition") 162 of the culture medium vessel 102, as illustrated in FIG. 1. The optical windows 105 and 106 may extend from, and/or terminate at, positions at which curvatures disposed along a xy-plane begin and end at a top section of the fillet 161 and/or a bottom section of the transition 162. Through the optical windows 105 and 106, parameters or conditions within the cell retention vessel 101 may be detected via sensors such as optical density sensors and spectroscopic sensors. The optical windows 105 and 106 may include transparent windows recessed from a top surface of the cell retention vessel 101, thereby permitting detection, through the optical windows 105 and 106, of biomass of cells within the cell retention vessel 101. For example, an amount or concentration of cells, cell density, cell diameter, and/or cell morphology may be detected through the optical windows 105 and 106, by non-invasive optical density sensors. Parameters of nutrients and metabolites may be determined through spectroscopic sensors. The optical windows 105 and 106 create a barrier between the spectroscopic sensors and analytes or metabolites in the culture medium while permitting transmission of optical signals from and back to the spectroscopic sensors.

Figure 3:
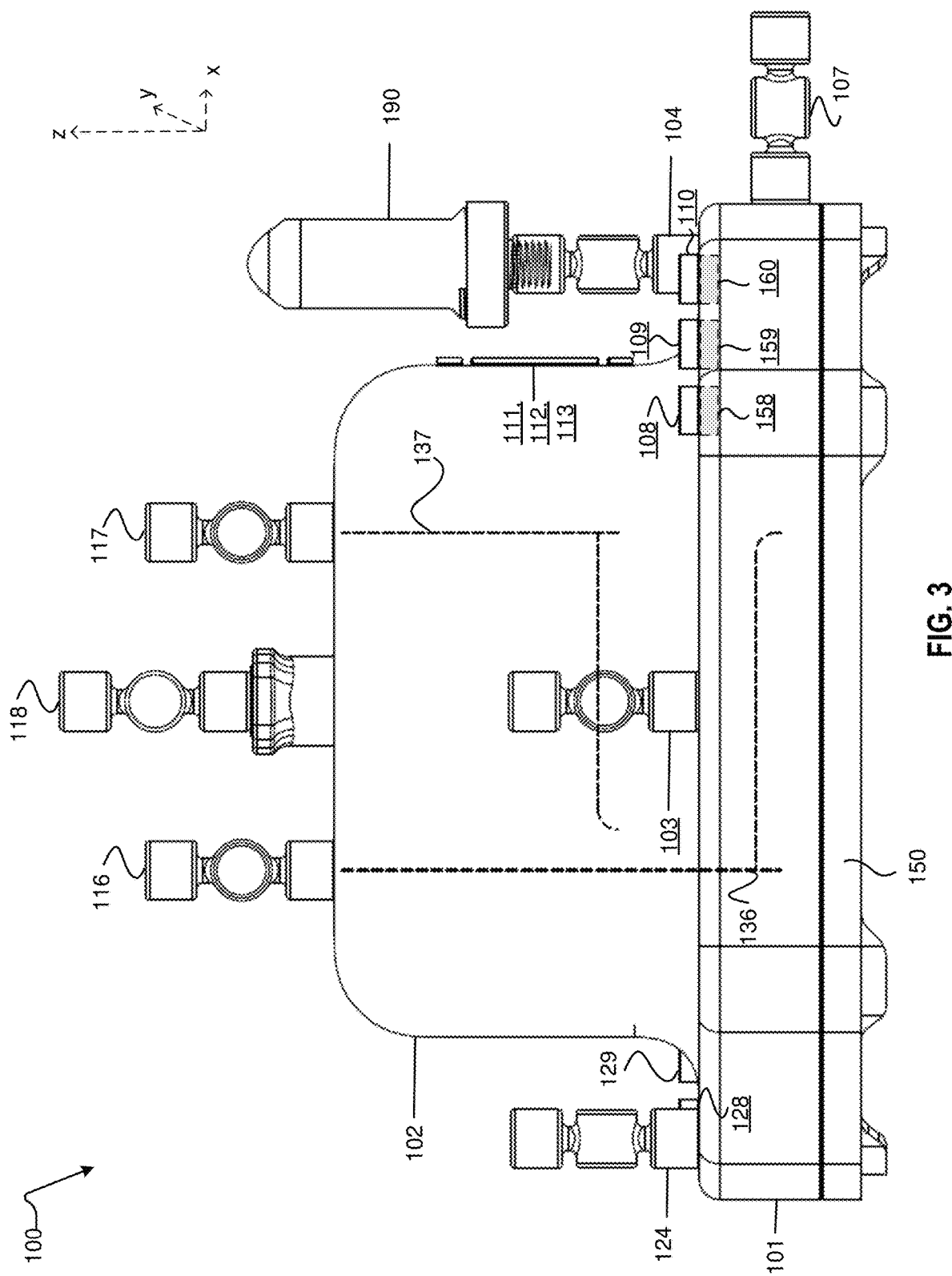
FIG. 3 illustrates an elevation, or orthographic, view of a front of an exemplary bioreactor, in accordance with various embodiments.
Figure 4:
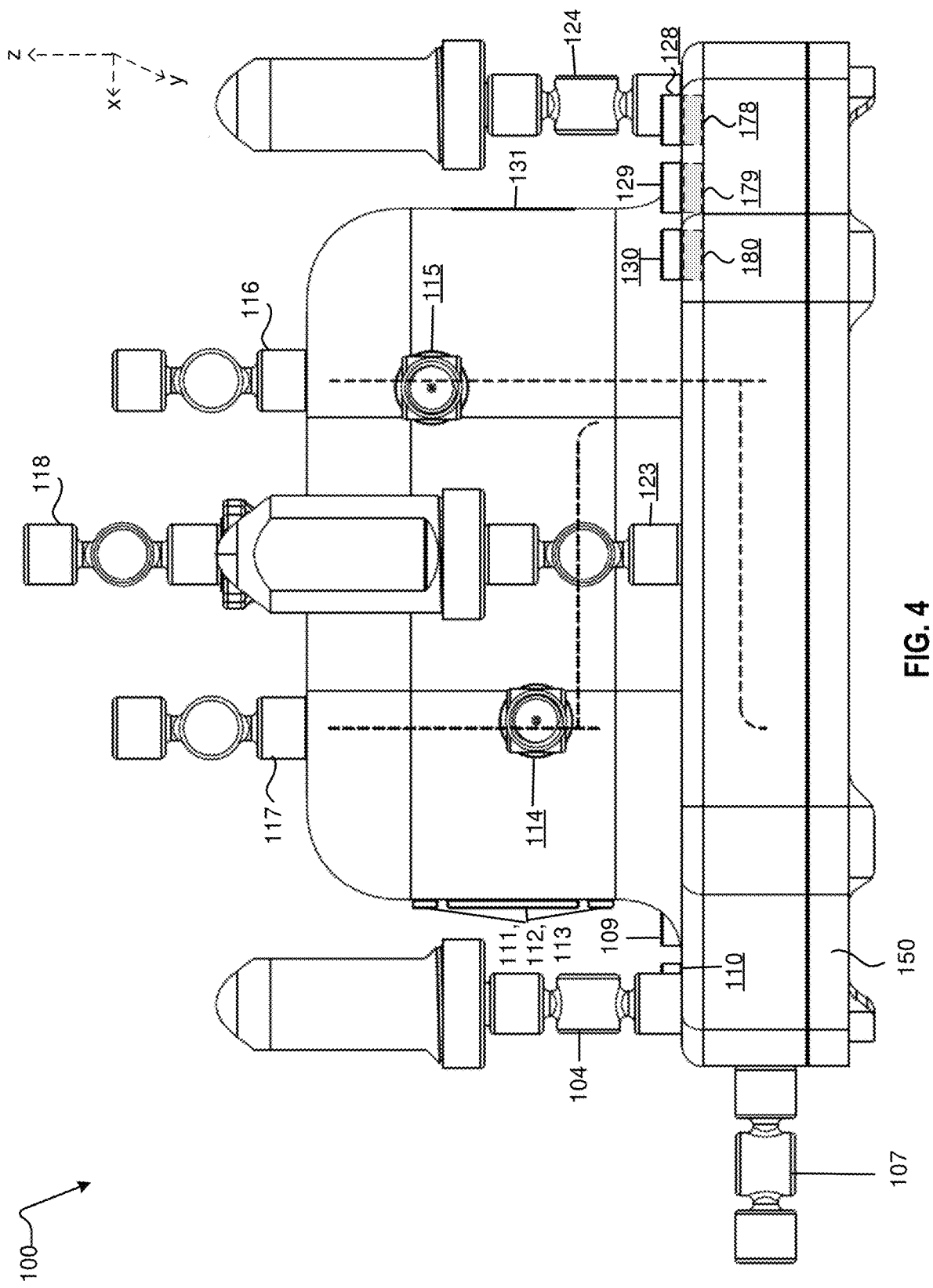
FIG. 4 illustrates an elevation, or orthographic, view of a back of an exemplary bioreactor, in accordance with various embodiments.
Figure 5:
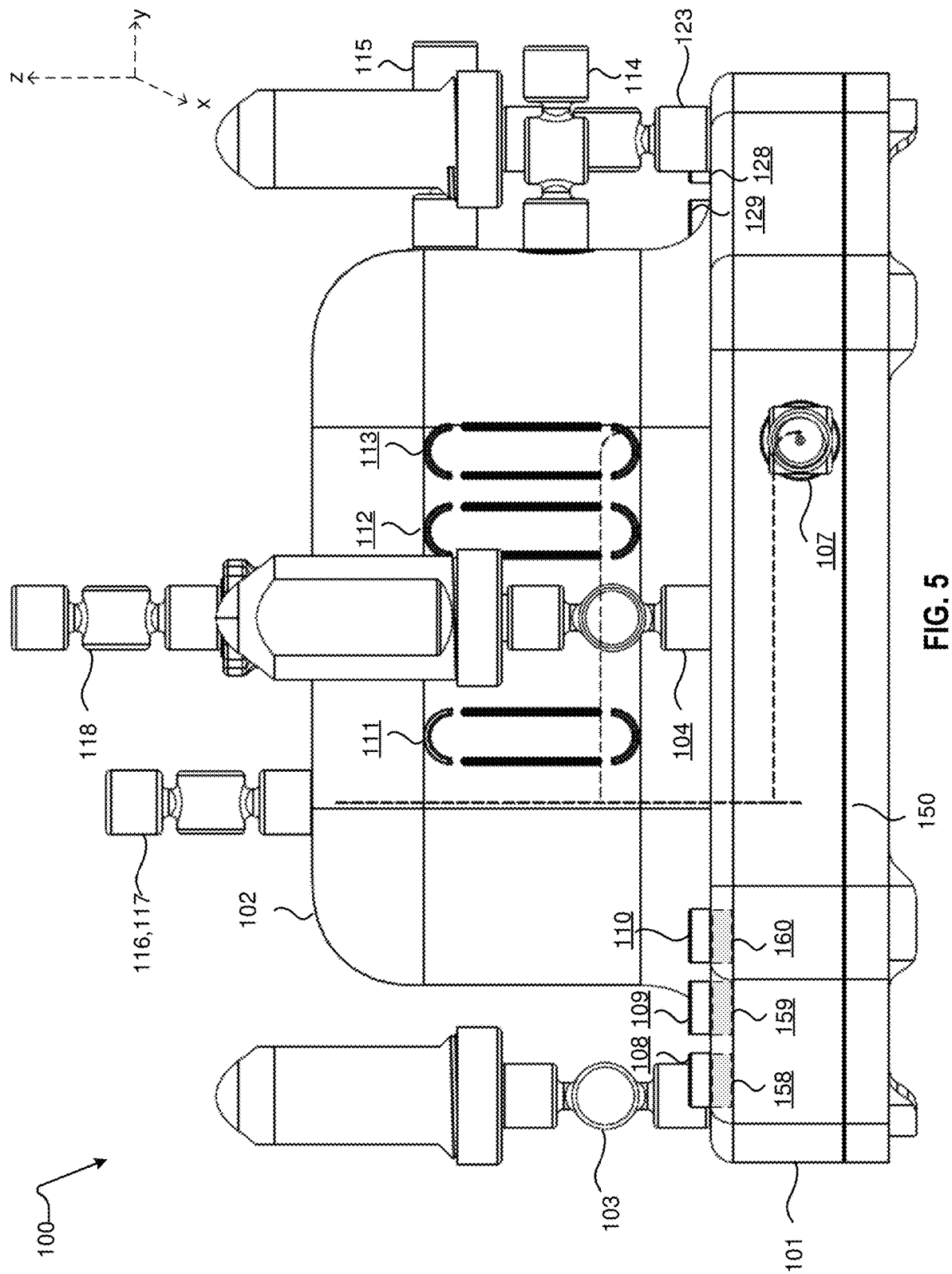
FIG. 5 illustrates an elevation, or orthographic, view of a right side of an exemplary bioreactor, in accordance with various embodiments.

Extending above the cell retention vessel 101, at a corner that is devoid of the optical windows 105 and 106, may be an array of sensor adapters 108, 109, and 110, as illustrated in FIGS. 1-6, 8-10, and 12. Although three sensor adapters 108, 109, and 110 are illustrated, any number of sensor adapters may be present, in part depending on how many sensor parameters are construed as CPPs and/or how many sensor parameters are to be measured. The sensor adapters 108, 109, and 110 may correspond to non-invasive FQS. In some embodiments, the sensor adapters 108, 109, and 110 may fix sensor spots 158, 159, and 160, respectively, or optical probes, at particular locations, as illustrated in FIG. 3 and FIG. 5. The sensor spots 158, 159, and 160 may be embedded within an interior of the cell retention vessel 101.

Figure 6:
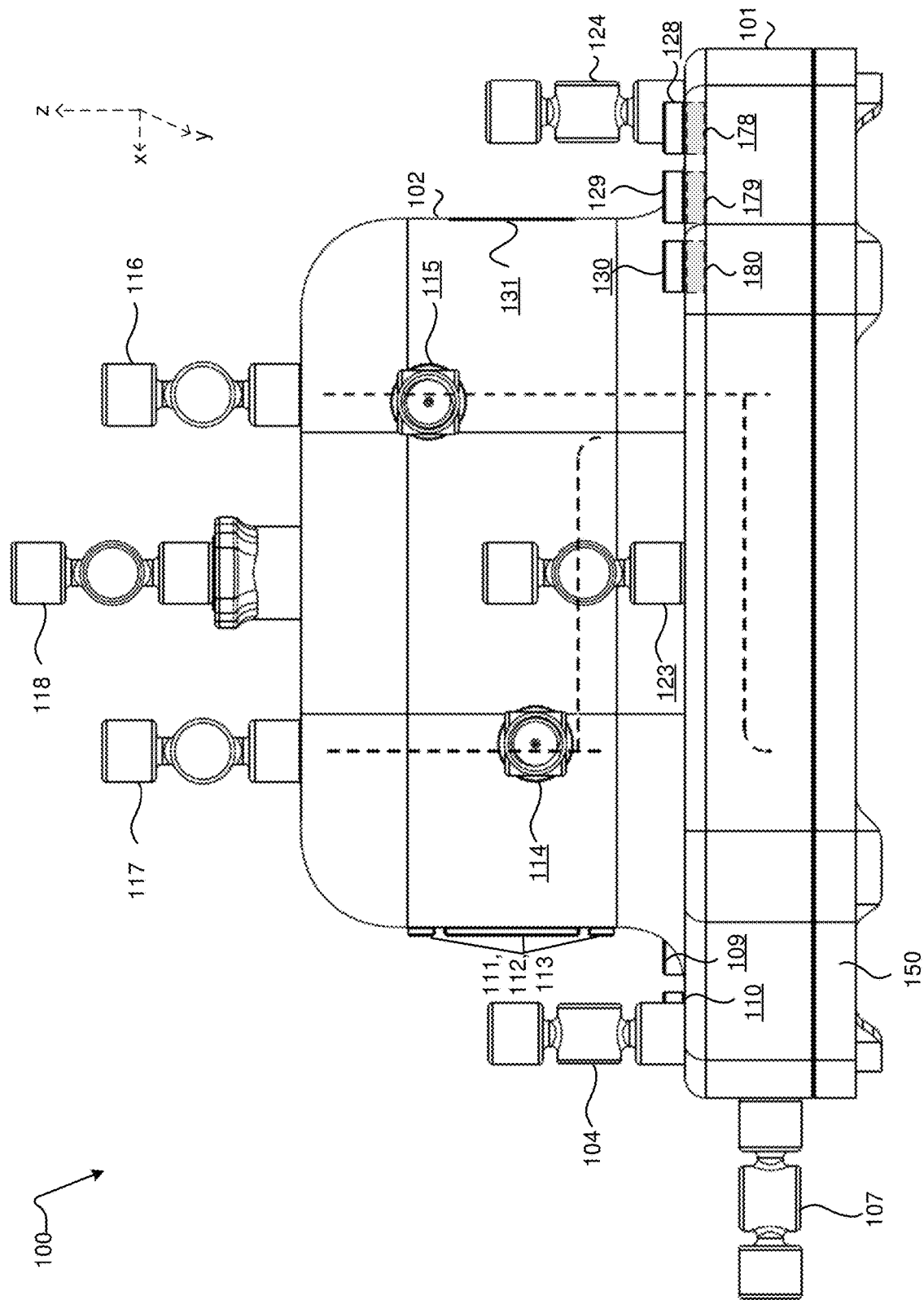
FIG. 6 illustrates an elevation, or orthographic, view of a right side of an exemplary bioreactor, in accordance with various embodiments.
Figure 7:
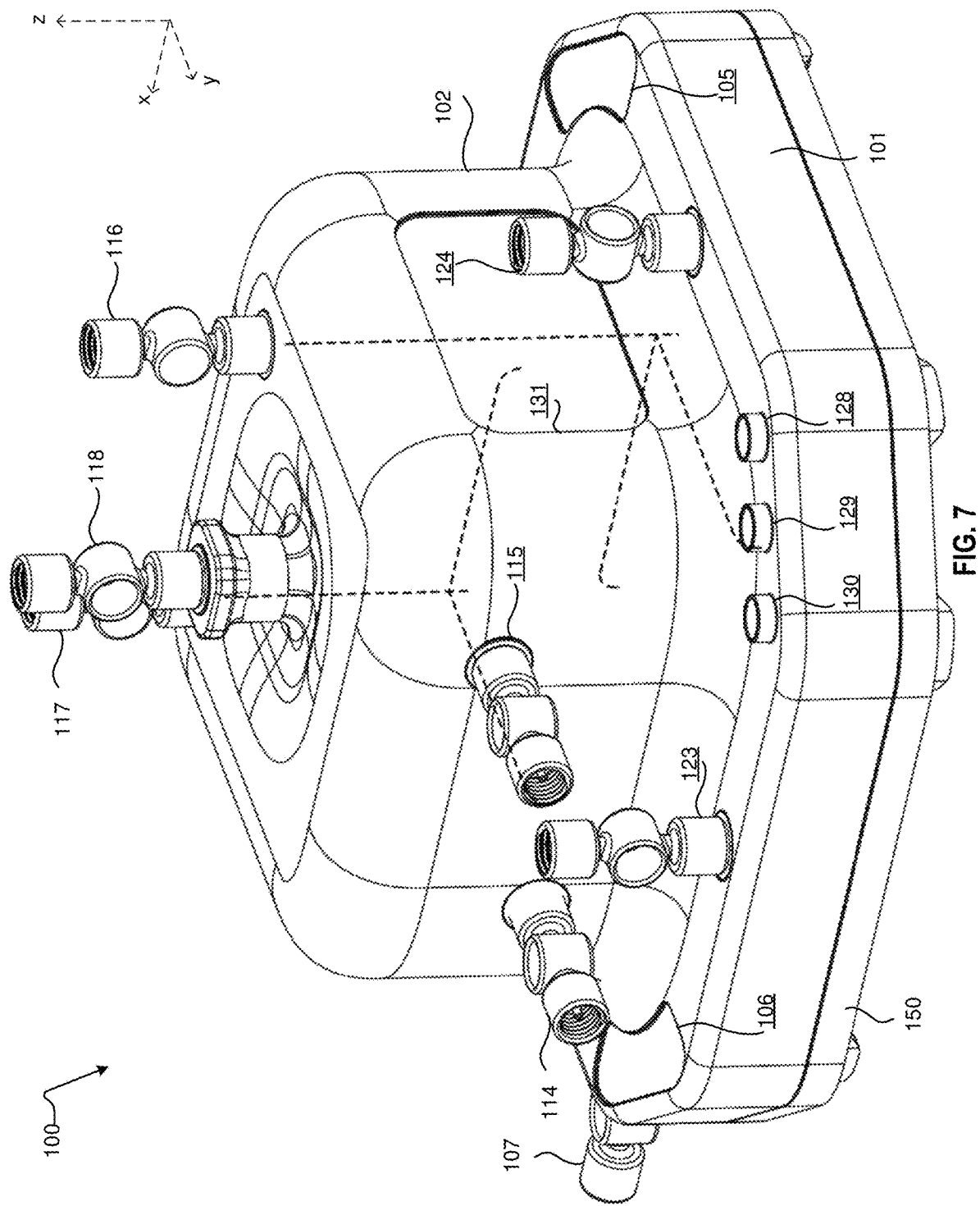
FIG. 7 illustrates a back perspective, or isometric, view of an exemplary bioreactor, in accordance with various embodiments.

Each of the optical probes corresponding to the sensor adapters 108, 109, and 110 may measure different parameters within the cell retention vessel 101 via technologies such as fluorescence quenching, as described above. For example, one of the optical probes may measure pH, while another may measure $pO_2$, and another may measure $pCO_2$. The optical probes fixed at the sensor adapters 108, 109, and 110 may be oriented along a xy-plane, to transmit signals along a negative z-direction from a top of the cell retention vessel 101 and receive signals along a positive z-direction from an interior of the cell retention vessel 101. The optical probes may have substantially circular or elliptical shapes. A width of each of the sensor adapters 108, 109, and 110 may be less than $w_1$, for example, between approximately 40% and 75% of $w_1$. The sensor adapters 108, 109, and 110 may each be spaced apart by a distance of between approximately 50% and 150% of $w_1$ so that the optical probes measure parameters around a common region while not overlapping or interfering with one another. Meanwhile, sensor adapters 128, 129, and 130 may have same or similar properties as the sensor adapters 108, 109, and 110, and may be disposed on opposite corners from the sensor adapters 108, 109, and 110, as illustrated in FIGS. 2-8 and 11. In some embodiments, the sensor adapters 128, 129, and 130 may fix sensor spots 178, 179, and 180, respectively, or optical probes, at particular locations, as illustrated in FIG. 4 and FIG. 6. The sensor spots 178, 179, and 180 may be embedded within an interior of the cell retention vessel 101. Therefore, any parameters measured by optical probes fixed to the sensor adapters 128, 129, and 130, and optical probes fixed to the sensor adapters 108, 109, and 110 at opposite corners of the cell retention vessel 101, may be averaged or selected using statistical methods.

Atop the cell retention vessel 101, at least one of cell injection interfaces 103, 104, 123, and 124 may connect to a tube, pipe, or other connector ("connector") to inject cells into the cell retention vessel 101. As alluded to above, the cell injection interfaces 103, 104, 123, and 124 may include Luer interfaces and/or threads. At least one of the cell injection interfaces 103, 104, 123, and 124 is illustrated in FIGS. 1-8 and 10-12. The cell injection interfaces 103, 104, 123, and 124 may connect or mate with a primary culture bioreactor, as described in U.S. patent application Ser. No. 17/459,156, hereby incorporated by reference in its entirely. Thus, the cell injection interfaces 103, 104, 123, and 124 may connect to ports through which cells that have already undergone an initial growth and proliferation stage (e.g., seed cells) are transported or imported into the cell retention vessel 101. If four cell injection interfaces 103, 104, 123, and 124 are atop the cell retention vessel 101, then the cell injection interfaces 103 and 123 are opposite each other, while the cell injection interfaces 104 and 124 are opposite each other. Having four cell injection interfaces 103, 104, 123, and 124 arranged symmetrically may balance a distribution of seed cells within the cell retention vessel 101 to prevent isolation or clumping of cells at one particular location. The balanced distribution of the seed cells may enhance cell yield and total cell density because distribution of nutrients and oxygen provided to the cells may also be balanced.

The cell injection interfaces 103, 104, 123, and 124 may extend a width $w_1$ of a flat portion on top of the cell retention vessel 101 between the fillet 161 and the transition 162, as illustrated in FIGS. 1 and 8. The cell injection interfaces 103, 104, 123, and 124 may have a circular or elliptical cross section both at respective tops and bottoms of the cell injection interfaces 103, 104, 123, and 124. The bottoms of the cell injection interfaces 103, 104, 123, and 124 may coincide with a top surface of the cell retention vessel 101. Each of the cell injection interfaces 103, 104, 123, and 124 may be disposed halfway between respective edges of the cell retention vessel 101. For example, respective centers of the cell injection interfaces 103 and 123 may have x-coordinates that are halfway between a smallest x-coordinate at an edge of the cell injection interface 103 and a largest x-coordinate at an opposite edge of the cell injection interface 103. Respective centers of the cell injection interfaces 104 and 124 may have y-coordinates that are halfway between a smallest y-coordinate at an edge of the cell injection interface 103 and a largest y-coordinate at an opposite edge of the cell injection interface 103.

In some embodiments, the process of cell injection is a continuous process in which a male Luer interface of the primary bioreactor, illustrated as a primary bioreactor 190 of FIG. 3, is reversed or translated to approach a complementary female Luer interface of one of the cell injection interfaces 103, 104, 123, and 124. The male Luer interface may be positioned onto the female Luer interface to complete a connection by tightening or screwing into a closed state. After the cell-free liquids containing cells and culture medium are injected into the cell retention vessel 101, the male Luer connection of the primary bioreactor 190 may be unlocked and released.

In some embodiments, contents from the primary bioreactor 190 may contain tissue impurities such as debris or tissue pieces which may impede a culturing process, thereby leading to potential contamination within the cell retention vessel 101 and additional filtration workload following cell harvest from the cell harvest interface 107. In an attempt to resolve this potential bottleneck, a filter apparatus may be positioned between a male Luer interface of the primary bioreactor 190 and the cell injection interface 104, as illustrated in FIG. 3. The filter apparatus may be positioned directly underneath a male Luer interface of the primary bioreactor 190. The filter apparatus may include a cylindrical container body beneath the male Luer interface, a membrane at a bottom of the cylindrical container body, and a male Luer interface of the primary bioreactor 190. A diameter of the membrane may be around 40 microns in some embodiments.

Along a side surface of the cell retention vessel 101, a cell harvest interface 107, as illustrated in FIGS. 1-8 and 10-12, may include a channel through which cells may be transmitted to a separate container once a level of proliferation within the cell retention vessel 101 has reached a threshold level of proliferation and/or parameters such as CPPs are determined to be within threshold ranges. Cell harvesting may correspond to a last stage following cell injection, medium exchange through interfaces of the culture medium vessel 102, which will be described in the subsequent description, and PAT analysis through the optical windows 105 and 106, the sensor adapters 108-110 and 128-130, and sensor adapters 111-113 of the culture medium vessel 102. In some embodiments, the cell harvest interface 107 may include a Luer lock port and a valve or other opening mechanism that remains closed until the cells reach a threshold level of proliferation. A pump, suction, and/or a passive transport mechanism either from the cell retention vessel 101 or from the separate container may divert or direct the cells from the cell retention vessel 101 into the separate container. Once the Luer lock port is opened, fluid inside the cell retention vessel 101 may flow through a connecting pipe, channel, tube, or conduit, downstream to a cell handling device (e.g., a centrifuge and/or larger container), for example, via gravity. The fluid flow may be stopped by locking the Luer lock port. The bioreactor 100 and the cell handling device may together constitute a closed system to protect the cells from the cell retention vessel 101 from cross-contamination with cells from other patients. Following cleaning, processing, and quality testing, the cells ejected from the cell harvest interface 107 may be injected into patients.

Unlike the cell injection interfaces 103, 104, 123, and 124, which are oriented along a z-axis, the cell harvest interface 107 may be oriented along an x-axis, as illustrated in FIGS. 1-8 and 10-12, or alternately, oriented along a y-axis. Although the cell harvest interface 107 is illustrated as extending from a right surface of the cell retention vessel 101, the cell harvest interface 107 may alternately extend from a left surface, a front surface, or a back surface of the cell retention vessel 101. The cell harvest interface 107 may be disposed beneath a top of the cell retention vessel 101, and/or beneath a top of a flat surface aligned along a xz-plane or an yz-plane of the cell retention vessel 101 to avoid excessive transport of cells against gravity because cells within the cell retention vessel 101 may not reach a top of the cell retention vessel 101.

Above the cell retention vessel 101, the culture medium vessel 102 may include between a negligible amount of culture medium and a full amount of culture medium, depending on growth requirements of nutrients and dissolved oxygen. CPPs and CQAs may be detected within the culture medium vessel 102 to avoid effects or interference from cells, as cells do not reside within the culture medium vessel 102. However, in some embodiments, samples may still be collected from the cell retention vessel 101, analyzed, and/or measured as a comparison and/or sanity check.

Interfaces within or connected to the culture medium vessel 102 may be used to facilitate injection of culture medium, collection or extraction of waste or excess culture medium, measurement of parameters such as CPPs, and/or extracting of samples. The interfaces and adapters within the culture medium vessel 102 may be a conduit through which representative samples are collected within the culture medium vessel 102 to obtain PAT data. The data corresponding to the culture medium vessel 102 may have different parameters and/or conditions compared to the cell retention vessel 101 because the cells reside within the cell retention vessel 101. Thus, the interfaces and adapters within the culture medium vessel 102 further complement those within the cell retention vessel 101 and further permit adjusting of parameters and/or conditions via injection of and/or extracting of substances within the culture medium vessel 102.

Disposed on a right-side wall of the culture medium vessel 102 are sensor adapters 111, 112, and 113, as illustrated in FIGS. 1-4, 6, 8, and 10. Although three sensor adapters 111, 112, and 113 are illustrated, any reasonable number of sensor adapters may be present, in part depending on how many sensor parameters are construed as CPPs and/or how many sensor parameters are to be measured. The sensor adapters 111, 112, and 113 may also correspond to the previously mentioned fluorescence quenching sensor spots 141, 142, and 143, respectively, as illustrated in FIG. 9. The sensor spots 141, 142, and 143 may be embedded inside the wall and may have substantially striped shapes.

In some embodiments, the sensor adapters 111, 112, and 113 may fix optical probes, for instance POFs, at particular locations. In some embodiments, the sensor adapters 111, 112, and 113 may enable manual or automatic movement of optical probes along a z-axis, depending on a height of the culture medium fluid. For example, if a height of the sensor adapters 111, 112, and 113 is too high, exceeding a level of the culture medium fluid, a height of the sensor adapters 111, 112, and 113 may be reduced. Each of the optical probes corresponding to the sensor adapters 111, 112, and 113 may measure different parameters within the culture medium vessel 102. For example, one of the optical probes may measure pH, while another may measure $pO_2$, and another may measure $pCO_2$. Optical probes fixed to the sensor adapters 111, 112, and 113 may transmit signals in a negative-x direction while receiving signals from a x-direction passing through the sidewall and sensor spots such as the sensor spots 141, 142, and 143. The optical probes fixed at the sensor adapters 111, 112, and 113 may be oriented along an yz-plane, to transmit signals along a negative x-direction from a right side of the culture medium vessel 102 and receive signals along a positive x-direction from an interior of the culture medium vessel 102. A height of each of the sensor adapters 111, 112, and 113 may be approximately 50% to 100% of a flat surface 163 within side walls of the culture medium vessel 102. The flat surface 163 may extend between the transition 162 to a rounded top 164, as illustrated in FIG. 1. A height (along a z-direction) of the flat surface 163 may range from between approximately 40% and 75% of a total height of the culture medium vessel 102, which may also include the transition 162 and the rounded top 164. By fixing the sensor adapters 111, 112, and 113 at a flat surface, rather than at a curved surface, the optical adapters may transmit and receive signals along a flat plane, thereby increasing a reliability of data collected, while additionally facilitating easy movement of the optical probes along the z-axis. The optical probes fixed to the sensor adapters 111, 112, and 113 may complement the optical probes fixed to the sensor adapters 108, 109, 110, and 128, 129, 130, by measuring parameters within the culture medium vessel 102. In some embodiments, as will be described with respect to FIG. 13, if corresponding parameters detected between the optical probes fixed to the sensor adapters 111, 112, and 113 and those fixed to the sensor adapters 108, 109, 110, and 128, 129, 130, differ by more than a threshold, the optical probes may remeasure the parameters and/or substances may be injected or expelled until the difference is within the threshold.

Disposed on a left surface, opposite to that of the sensor adapters 111, 112, and 113, may be an optical window 131, as illustrated in FIGS. 4, 6, 7, 11, and 12. The optical window 131 may be shaped differently from the optical windows 105 and 106. The optical window 131 may extend a portion of, or an entirety of, a left side of the flat surface 163 between the transition 162 and the rounded top 164. The optical window 131 may be coplanar with the flat surface 163 or may be recessed into the flat surface 163. Through the optical window 131, parameters or conditions within the culture medium vessel 102 may be imaged or detected via sensors such as optical density sensors, fluorescence quenching sensors (FQS) and spectroscopic sensors, as described with respect to FIG. 13.

Disposed on a back surface of the culture medium vessel 102 may be waste collection interfaces 115 and 114, as illustrated in FIGS. 1, 2, and 4-11. The waste collection interfaces 115 and 114 may remove excess, waste, used and/or detrimental culture medium from the culture medium vessel 102, for example, prior to injection of fresh culture medium and cell harvest. The waste collection interfaces 115 and 114 may be attached to a pump, a valve and/or other actuating mechanism such as an automated or robotic system (hereinafter "valve"). The valve may be opened to permit the egress of the excess growth media based on parameters detected within the culture medium vessel 102 and/or the cell retention vessel 101. In some embodiments, for example, if certain parameters are outside of threshold or permissible ranges, then the valve may be opened. Otherwise, the valve may remain closed or sealed. Such actuation or activation of the valve may be performed electronically. The waste collection interface 114 may be positioned lower, with respect to a z-axis, compared to the waste collection interface 115. If a fluid level within the culture medium vessel 102 is high enough, excess growth media may be ejected or funneled through one or both of the waste collection interfaces 115 and 114. If a fluid level within the culture medium vessel 102 fails to reach a height of the waste collection interface 115, excess culture medium may be ejected or funneled through the waste collection interface 114. Therefore, having two waste collection interfaces 114 and 115 may permit ejection or funneling of culture medium even at variable heights of the culture medium. The waste collection interfaces 114 and 115 may be positioned at a flat surface 163 of the culture medium vessel 102, or at least partially at a curved section 165 of the culture medium vessel 102. In some embodiments, culture medium may be ejected via the waste collection interfaces 115 and/or 114 prior to injection of fresh culture medium through a culture medium injection interface 118 and/or cell harvest through a cell harvest interface 107.

Additionally, the culture medium injection interface 118, and sampling interfaces 116 and 117, may extend and/or be immobilized above the culture medium vessel 102 along a z-direction, as illustrated in FIGS. 1-12. The culture medium injection interface 118 may connect or mate to a connector such as a male Luer connector through which fresh culture medium is injected from the connector of an external device such as a pipette, automated pipette, or pump-based medium transfer apparatus or machine. Fresh culture medium may be injected into the culture medium injection interface 118 via an automated process which also determines an amount of fresh culture medium to be injected. In some embodiments, prior to fresh culture medium injection, used or waste culture medium may be expelled from the culture medium vessel 102, via the waste collection interfaces 114 and 115. In some embodiments, prior to cell harvest, used or waste culture medium may be expelled from the culture medium vessel 102, via the cell harvest interface 107. In some embodiments, an additional impeller may be inserted into the medium injection interface 118 in order to mix the cells and/or culture medium. In some embodiments, an additional rocking platform may be placed underneath the bioreactor in order to mix the cells and/or culture medium via a proper extend of rotation or vortex.

The culture medium injection interface 118 may be disposed at a center of the culture medium vessel 102. A pipe may extend into the culture medium injection interface 118. The connector may include or be connected to a channel 138, as illustrated in FIG. 9, which may extend into the culture medium vessel 102, to a bottom of the culture medium vessel 102, and/or into the cell retention vessel 101. As illustrated, for example, in FIG. 8, the culture medium injection interface 118 may be aligned with the cell injection interfaces 104 and 124 in a y-direction. In other words, y-coordinates of the culture medium injection interface 118 may match y-coordinates of the cell injection interfaces 104 and 124. The culture medium injection interface 118 may be aligned with the cell injection interfaces 103 and 123 in a x-direction, meaning that x-coordinates of the culture medium injection interface 118 may match x-coordinates of the cell injection interfaces 103 and 123.

Sampling interfaces 116 and 117 may be offset in a negative-y direction with respect to the culture medium injection interface 118. As illustrated in FIG. 8, assume a distance in a y-direction from the culture medium injection interface 118 to an edge of a flat portion (e.g., a section parallel to a xy-plane) of a top of the culture medium vessel 102 is $w_2$, a distance in a y-direction from the sampling interface 116 to the edge of the flat portion is $w_3$, and a distance in a y-direction from the sampling interface 117 to the edge of the flat portion is $w_4$. in some embodiments, $w_3$ and $w_4$ may be equal or different. In some embodiments, $w_3$ and/or $w_4$ may be half of, less than half of, or greater than half of $w_2$.

The sampling interface 116 may be offset in a negative-x direction with respect to the culture medium injection interface 118. As illustrated in FIG. 8, assume a distance in a x-direction from the culture medium injection interface 118 to a left edge of a flat portion (e.g., a section parallel to a xy-plane) of a top of the culture medium vessel 102 is $I_2$, a distance in a x-direction from the culture medium injection interface 118 to a right edge of a flat portion (e.g., a section parallel to a xy-plane) of a top of the culture medium vessel 102 is $I_4$, a distance in a x-direction from the sampling interface 116 to the left edge of the flat portion is $I_1$, and a distance in a x-direction from the sampling interface 117 to the right edge of the flat portion is $I_3$. in some embodiments, $I_2$ and $I_4$ may be equal or different. In some embodiments, $I_1$ may be half of, less than half of, or greater than half of $I_2$. In some embodiments, $I_3$ may be half of, less than half of, or greater than half of $I_4$. Thus, the sampling interfaces 116 and 117, and the culture medium injection interface 118, may be spaced apart sufficiently so that channels through the sampling interfaces 116 and 117, and the culture medium injection interface 118, do not interfere with one another, and the sampling interfaces 116 and 117, and the culture medium injection interface 118, are not positioned too close to an edge of the culture medium vessel 102.

In some embodiments, the sampling interface 116 may connect or mate to a connector such as a male Luer connector of a pump, valves, and/or integrated PAT analyzers used to extract representative samples from the cell retention vessel 101 to downstream PAT analysis module. The connector may include or be connected to a pipe or channel 136, as illustrated in FIGS. 3 and 12, which may extend into the cell retention vessel 101 in order to collect samples of cell-free media from the cell retention vessel 101 for analysis. The analysis may involve PAT analysis of attributes such as a total cell density, viable cell density, cell concentration, cell diameter, and/or cell morphology. The channel 136 may be bifurcated into multiple branches, such as four branches so that samples from different locations may be taken to reduce or eliminate potential bias at a single sampling location. In some embodiments, the sampling interface 117 may connect or mate to a connector such as a male Luer connector of a pump, valves and/or integrated PAT analyzers used to extract representative liquid samples from the culture medium vessel 102 to downstream PAT analysis module. The connector may include or be connected to a pipe or channel 137, as illustrated in FIGS. 3, 9, and 12, which may extend into the culture medium vessel 102 in order to collect a sample of growth media from the culture medium vessel 102 for analysis. Similar to the channel 136, the channel 137 may be bifurcated into multiple branches, such as four branches so that samples from different locations may be taken to reduce or eliminate potential bias at a single location. Therefore, samples may specifically be extracted from both the cell retention vessel 101 and the culture medium vessel 102 at a same time and compared. As will be described with respect to FIG. 13, if corresponding parameters within the culture medium vessel and the cell retention vessel 101 deviate by more than a threshold amount, then additional samples from the cell retention vessel 101 and the culture medium vessel 102 may be extracted, measured, and analyzed. Using Luer interfaces at both the sampling interfaces 116 and 117 may ensure the combination of the bioreactor 100 and external PAT analyzers forms a complete closed system, in which a leakage of samples back into the culture medium vessel 102 and to a clean chamber may be prevented, and cross-contaminations of different patients may be avoided if incubated in a same clean chamber or GMP (Good Manufacturing Practice) room. Therefore, the closed system allows the viability of simultaneously incubating and expanding cells from multiple patients inside one clean room, which increases the efficiency of GMP-compliance, and decrease the costs of building isolated clean rooms.

FIG. 13 illustrates a systematic process of PAT-based analysis and decision-making by which growth conditions within the bioreactor, may be seamlessly understood and adjusted. In particular, raw data or parameters 1302 (hereinafter "raw data") for PAT data analysis may be acquired through any of optical probes, sensor spots such as the sensor spots 158, 159, 160, 178, 179, 180, 141, 142, and/or 143, or connected external PAT analyzers which correspond to the sensor adapters 111, 112, 113, 108, 109, 110, 128, 129, 130, the optical windows 105, 106, and 131, and/or sampling interfaces 116 and 117. A processor 1310 may receive raw data or metadata of multiple parameters. The processor 1310 may conduct PAT analysis and/or decision-making regarding cells and culture medium parameters or conditions. For example, the processor 1310 may determine a status of culture medium expulsion or injection. The status may include whether or not the culture medium is to be injected or expelled or a precise batch at which the culture medium is to be injected or expelled. Additionally or alternatively, the processor 1310 may determine a status of a cell harvest or a cell injection. The status may include whether or not the cells are to be harvested or extracted, or additional seed cells are to be injected, or a timepoint at which the cells are to be harvested or extracted, or additional seed cells are to be injected. The processor 1310 may decide or determine the consistent supervision and discrete remeasurement of specific parameters which are abnormal or imprecise by utilizing underlying sensors, according to the results of PAT analysis. Meanwhile, a processor 1320 may perform determination and/or actuation of components 1330 to adjust connectors to aforementioned interfaces of FIGS. 1-12, such as connectors of the cell harvest interface 107, the cell injection interfaces 103, 104, 123, and 124, the culture medium injection interface 118, and/or the waste collection interfaces 114 and 115. The processor 1320 may receive inputs from the processor 1310, raw data for PAT analysis, processed data and/or metadata. In some embodiments, the processors 1310 and 1320 may be integrated and not spatially separated. For example, functions delegated to the processors 1310 and 1320 may be performed by a common processor.

As an example, if the biomass reaches a threshold value or range, then the processor 1310 may determine that cells are to be harvested through the cell harvest interface 107. The processor 1320 may actuate or manipulate components 1330, as will be described subsequently, in order to open a channel, pipe, or conduit through the cell harvest interface 107. The cells may be transported into an incubator or a larger container. In some embodiments, parameters of pH, $pO_2$, and $pCO_2$ are detected to obtain a chemical state of the culture medium. Determinations regarding whether to inject culture medium and/or expel culture medium, and specific times, amounts or rates at which culture medium is injected or expelled, may be based on the parameters. For example, if a pH is less than 7.2, part of the culture medium within the bioreactor 100 may be funneled through the waste collection interfaces 114 and/or 115, while fresh culture medium may be injected via the culture medium injection interface 118 to readjust the pH to a normal range, such as between 7.2 and 7.4, inclusive. Additionally or alternatively, if $pO_2$, and $pCO_2$ are also supporting indicators to determine steps of injecting culture medium and/or expelling culture medium. For example, if $pO_2$ is lower than a threshold and $pCO_2$ is higher than a second threshold, then a timing of injection of the culture medium may be expedited, and/or amounts or rates at which the culture medium is injected may be increased. Moreover, nutrients and metabolites including glucose, glutamine, glutamate, lactate, ammonium, ethanol, are further parameters to determine the volume of culture medium to be injected especially in fed-batch culture mode.

The monitoring of biomass, pH, $pO_2$, and $pCO_2$, and nutrients and metabolites may be conducted via three types of PAT sensors or systems, including an optical density sensor, fluorescence quenching sensor, and a spectroscopic sensor, which may be implemented consistent with previous FIGS. 1-12. An optical density sensor may be a non-invasive sensor to detect the biomass, employing a principle of optical density to detect a turbidity of a suspension. An optical density sensor can translate or slide to different detection positions on an optical window, such as the optical window 105, 106, or 131, to acquire parameters at different locations within the culture medium vessel 102 and cell retention vessel 101. The parameters at the different locations may be averaged or selected using statistical methods. The optical density sensor may be removed from the optical window, returned to a sensor rack, and reused following detection.

Meanwhile, Fluorescence Quenching Sensors (FQS), may detect pH, $pO_2$, and $pCO_2$, or other related parameters. The FQS may include any of disposable sensor spots, a POF, and an optical meter. Disposable sensor spots including six rounded or cylindrical sensor spots 158, 159, 160, 178, 179, and 180, as illustrated in FIGS. 3-6, and three striped sensor spots 141, 142, 143, as illustrated in FIG. 9, may be embedded inside the wall of vessels such as the cell retention vessel 101 or the culture medium vessel 102. In contrast, a POF and optical meter may be positioned outside the bioreactor 100. A POF, functioning as a detector, may be positioned at a sensor adapter, such as the sensor adapter 111, 112, or 113, corresponding to a particular sensor spot, inserted into the sensor adapter, and afterward disconnected from the adapter and returned to the sensor rack after detection. The sensor adapters 111, 112, and 113 of the culture medium vessel may be in a shape of a rounded rectangle. Therefore, a mechanism to detect the pH, $pO_2$, and $pCO_2$ in the culture medium vessel 102 may be different from a mechanism to detect the pH, $pO_2$, and $pCO_2$ in the cell retention vessel 101. In particular, the POF may capture a wider region of detectable substances within the culture medium vessel 102. Thus, the POF, or FQS is manipulated to slide up and down to a specific coordinate or location within the sensor adapter 111, 112, or 113, to continuously capture results at different vertical levels or heights corresponding to z-axis coordinates of the culture medium vessel 102. In such a manner, the analysis of biological conditions or parameters within the culture medium vessel 102 may be more balanced by obtaining results at different z-axis coordinates, which facilitates increased precision of PAT-aided decision-making and improved cell density and uniformity of cells.

Spectroscopic sensors may non-invasively detect complex attributes, parameters, or conditions of nutrients and metabolites. Spectroscopic sensors may be similar to optical density sensors. The spectroscopic sensors may be translated to vertically contact the optical window 131, detect the attributes, parameters, or conditions, and returned to the sensor rack. The spectroscopic sensors staying outside the closed system do not contact the culture medium at any time, so that they may be reusable for other expansive iterations of clinical patients.

Besides the above introduced sensors, the bioreactor 100 may further support a comprehensive or integrated method of monitoring parameters, via utilization of PAT analyzers as external devices to analyze the extracted samples, such as from the sampling interfaces 116 and 117 from the bioreactor 100 to conduct in-line analysis. The PAT analyzers may include pumps, valves, disposable dialysis probes, bypass modules, filtration probes, and advanced computing system. In particular, the PAT analyzers may implement precise and stable capability in terms of liquid sample processing, calculation and analysis. In conjunction with the three types of aforementioned sensors, the optical density sensors, the fluorescence sensors, and the spectroscopic sensors that non-invasively detect independent and controllable variables, parameters, or conditions, the PAT analyzers may be synchronized as a multimodal method of PAT framework to satisfy precise and flexible requirements of understanding, controlling, and optimizing the bioprocess of cell expansion.

In some embodiments, the processor 1310 may participate in a PAT-aided analysis which involves monitoring of conditions and parameters, calculating, visualizing and interpreting results or data, and decision-making. The processor 1310 may include hardware deployed as a basis of the PAT-aided analysis. The processor 1310 may receive data from smart sensors including the PAT sensors. The processor may include the machine learning-based predictive models or deep learning models. The processor 1310 may be integrated as part of a network that includes local and cloud servers, routers, power supplies, network devices, and/or client devices. The processor 1310 may communicate with the smart sensors and/or the processor 1320 via protocols such as Bluetooth, Wi-Fi, or TCP/IP protocols. The processor 1310 may implement machine learning and/or artificial intelligence (AI)-aided analysis and decision-making to determine precise liquid handling conditions or parameters based on on-line and in-line PAT monitoring and analysis to acquire a global perspective of a bioprocess associated with cell growth and proliferation. The processor 1310 uses an iterative method through continuous monitoring, analysis, adjusting of growth parameters or conditions, and injection or ejection of culture medium, to improve cell density, quality, and efficacy.

In some embodiments, the processor 1320 may control components 1330 which may include or be part of an automated or robotic system. The control or actuation using the components 1330 may either based on data analysis from the processor 1310. In some embodiments, the components 1330 may be involved in a movement or manipulation of physical tools including bioreactors, sensors, accessories, the connection of Luer ports and the external devices, the interaction of three types of PAT sensors and the sensor adaptors or optical windows, and operations of external devices such as the PAT analyzer. Manipulations and movements may be in accordance with automated protocols and/or pipelines. Particular examples of manipulations or movements by the components 1330 may include, for example, switching on or off valves, connectors or actuators of the cell harvest interface 107, the cell injection interfaces 103, 104, 123, and 124, the culture medium injection interface 118, and/or the waste collection interfaces 114 and 115, moving sensors from sensor racks and positioning the sensors onto sensor adapters, connecting I/O Luer interfaces to common ports of external devices such as containers, incubators, pipettes, PAT analyzers, and/or impellers, manipulating non-invasive sensors for online monitoring, and/or connecting or dispatching primary bioreactors such as the primary bioreactor 190 to or from a cell injection interface such as the cell injection interface 103, 104, 123, or 124.

In some examples, if an analysis reveals, suggests, or indicates that a cell density is below a threshold, and/or that cell morphology is abnormal (e.g., a deviation in a parameter, and/or a parameter of the cells, such as width, is outside of a threshold), then the components 1330 may control connectors associated with the culture medium injection interface 118 to inject additional culture or growth medium into the bioreactor 100, and/or increase a rate of injection. In addition, the components 1330 may further increase an amount of oxygen flowing into the grid of the support 150. If, on the other hand, the analysis reveals, suggests, or indicates that the cell density is above a threshold, then the components 1330 may control connectors associated with the culture medium injection interface 118 to extract a culture medium from the base 100 via the waste collection interfaces 114 and/or 115. In some examples, if a cell density has reached a threshold, then the components 1330 may control connectors associated with the cell harvest interface 107 to extract cells. The components 1330 may open valves or actuators associated with the waste collection interfaces 114 and/or 115, and/or the cell harvest interface 107 depending on conditions or parameters.

FIG. 14 illustrates a block diagram of a computing system 1400 upon which any of the embodiments described herein may be implemented. The computer system 1400 includes a bus 1402 or other communication mechanism for communicating information, one or more hardware processors 1404 coupled with bus 1402 for processing information. The hardware processors 1404 may be implemented and deployed at edge side, for example, as any of the processors 510, 420, or 320. The computing system 1400 also includes a main memory 1406, such as a random-access memory (RAM), cache and/or other dynamic storage devices, coupled to bus 1402 for storing information and instructions to be executed by processor 1404. Main memory 1406 also may be used for storing temporary variables or other intermediate information during execution of instructions to be executed by the hardware processors 1404. Such instructions, when stored in storage media accessible to the hardware processors 1404, render computer system 1400 into a special-purpose machine that is customized to perform the operations specified in the instructions.

The computing system 1400 further includes a read only memory (ROM) 1408 or other static storage device coupled to bus 1402 for storing static information and instructions for processor 1404. A storage device 1410, such as a magnetic disk, optical disk, or USB thumb drive (Flash drive), etc., is provided and coupled to bus 1402 for storing information and instructions. The computing system 1400 may be coupled via bus 1402 to output device(s) 1412, such as a cathode ray tube (CRT) or LCD display (or touch screen), for displaying information to a computer user who may be the cell culture operator or lab manager. Input device(s) 1414 deployed at the cloud or remote ends outside the operating clean room, including alphanumeric and other keys, are coupled to bus 1402 for remotely communicating information and command selections to the hardware processors 1404. Another type of user input device is cursor control 1416. The computing system 1400 also includes an interactive human-machine or human-robot interface 1418 coupled to bus 1402.

Unless the context requires otherwise, throughout the present specification and claims, the word "comprise" and variations thereof, such as, "comprises" and "comprising" are to be construed in an open, inclusive sense, that is as "including, but not limited to." Recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a," "an" and "the" include plural referents unless the context clearly dictates otherwise. The phrases "at least one of," "at least one selected from the group of," or "at least one selected from the group consisting of," and the like are to be interpreted in the disjunctive (e.g., not to be interpreted as at least one of A and at least one of B).

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment but may be in some instances. Furthermore, the particular features, structures, or characteristics may be combined in any suitable manner in one or more embodiment. A component being implemented as another component may be construed as the component being operated in a same or similar manner as another component, and/or comprising same or similar features, characteristics, and parameters as another component.

What is claimed is:

1. A bioreactor comprising:
   optical sensors, wherein the optical sensors are fixed and determine conditions or parameters comprising a pH, a partial pressure of dissolved oxygen ($pO_2$), and a partial pressure of dissolved carbon dioxide ($pCO_2$) within a culture medium vessel;
   the culture medium vessel housing culture medium, the culture medium vessel further comprising:
   a first side surface comprising a first transparent optical window; and
   a second side surface parallel to the first side surface and comprising one or more sensor adapters to fix the optical sensors;
   a cell retention vessel disposed underneath and connected to the culture medium vessel, the cell retention vessel housing biological cells and comprising:
   a top surface that intersects a base of the culture medium vessel; and
   a second transparent optical window indented into the top surface at a first corner of the top surface;
   a semipermeable membrane disposed at a bottom of the cell retention vessel; and
   a frame comprising a grid disposed underneath the semipermeable membrane;
   waste collection interfaces comprising respective connectors;
   valves attached to the respective connectors, wherein the valves are electronically controlled, by a processor, to automatically open and close based on the conditions or parameters; and
   tubes or pipes attached to the valves through which a portion of the culture medium is expelled upon opening of the valves.

2. The bioreactor of claim 1, wherein the cell retention vessel has a larger width and a smaller height compared to the culture medium vessel in order to support a larger surface area on which the biological cells grow.

3. The bioreactor of claim 1, wherein the culture medium vessel comprises third side surfaces from which interfaces extend, wherein the third side surfaces are parallel to each other and orthogonal to the first side surface and the second side surface.

4. The bioreactor of claim 3, wherein the interfaces extending from the third side surfaces comprise Luer connectors.

5. The bioreactor of claim 3, wherein the interfaces extending from the third side surfaces comprise one or more waste collection interfaces through which culture medium is expelled.

6. The bioreactor of claim 1, wherein the cell retention vessel comprises one or more second sensor adapters extending from the top surface of the cell retention vessel, wherein the second sensor adapters are configured to fix second optical sensors.

7. The bioreactor of claim 1, wherein the optical sensors comprise fluorescence quenching sensors vertically translatable along the sensor adapters.

8. The bioreactor of claim 1, wherein the culture medium vessel further comprises:
   a top surface; and
   extending from the top surface, a culture medium injection interface through which culture medium is injected into the culture medium vessel.

9. The bioreactor of claim 1, wherein the culture medium vessel further comprises:
   extending from the top surface, one or more sampling interfaces from which samples within the culture medium vessel or the cell retention vessel are extracted for in-line process analytical technology (PAT) analysis.

10. The bioreactor of claim 9, wherein the sampling interfaces comprise a first sampling interface from which a sample within the culture medium vessel is extracted and a second sampling interface from which a sample within the cell retention vessel is extracted.

11. The bioreactor of claim 1, wherein an interior of the bottom of the culture medium vessel is hollowed, the interior of the bottom of the culture medium vessel coinciding with an interior portion of the top surface of the cell retention vessel.

12. The bioreactor of claim 1, wherein the cell retention vessel further comprises:
   a side surface; and
   extending from the side surface, a cell harvest interface from which a subset of the biological cells is transferred to be harvested upon a threshold concentration of the biological cells being detected within the cell retention vessel.

13. The bioreactor of claim 1, wherein the cell retention vessel further comprises:
   extending from the top surface of the cell retention vessel, cell injection interfaces through which the biological cells are injected into the cell retention vessel.

14. The bioreactor of claim 13, wherein the top surface of the cell retention vessel comprises four orthogonal sides and a hollowed interior region to an interior of the bottom of the culture medium vessel; and the cell injection interfaces are disposed on different sides of the top surface of the cell retention vessel.

15. The bioreactor of claim 1, wherein at least a portion of the valves open in response to the pH being lower than approximately 7.2 and closes in response to the pH being between 7.2 and 7.4.

16. The bioreactor of claim 1, further comprising:
   culture medium injection interfaces comprising respective second connectors;
   second valves attached to the respective second connectors, wherein the second valves automatically open and close based on the pH, the $pO_2$, and the $pCO_2$; and
   second tubes or second pipes attached to the second valves through which additional culture medium is injected upon opening of the second valves.

17. The bioreactor of claim 16, wherein at least a portion of the second valves open in response to the $pO_2$ being lower than a second threshold and the $pCO_2$ being lower than a third threshold.

18. The bioreactor of claim 16, wherein the second valves automatically open and close further based on a concentration of any three of glucose, glutamine, glutamate, lactate, ammonium, and ethanol.

19. The bioreactor of claim 1, wherein the waste collection interfaces are at different heights along a flat surface of the culture medium vessel.

20. The bioreactor of claim 1, wherein the optical sensors further determine a concentration of viable cells, a diameter, and a morphology of cells in the culture medium vessel; and the bioreactor further comprising:
   a cell harvest interface comprising a third connector;
   a third valve attached to the third connector, wherein the third valve automatically opens and closes based on the concentration of viable cells, the diameter, and the morphology; and
   third tubes or third pipes attached to the third valve through which the culture medium is diverted upon opening of the third valve.

* * * * *